United States Patent
Walker et al.

(10) Patent No.: US 6,660,269 B2
(45) Date of Patent: Dec. 9, 2003

(54) **HOMOLOGOUS 28-KILODALTON IMMUNODOMINANT PROTEIN GENES OF *EHRLICHIA CANIS* AND USES THEREOF**

(75) Inventors: David H. Walker, Galveston, TX (US); Xue-Jie Yu, Houston, TX (US); Jere W. McBride, Galveston, TX (US)

(73) Assignee: Research Development Foundation, Carson City, NV (US)

( * ) Notice: Subject to any disclaimer, the term of this patent is extended or adjusted under 35 U.S.C. 154(b) by 122 days.

(21) Appl. No.: 09/811,007

(22) Filed: Mar. 16, 2001

(65) Prior Publication Data

US 2003/0185849 A1 Oct. 2, 2003

Related U.S. Application Data

(60) Division of application No. 09/660,587, filed on Sep. 12, 2000, now Pat. No. 6,392,023, which is a continuation-in-part of application No. 09/261,358, filed on Mar. 3, 1999, now Pat. No. 6,403,780, which is a continuation-in-part of application No. 09/201,458, filed on Nov. 30, 1998, now Pat. No. 6,458,942.

(51) Int. Cl.[7] .................. A61K 39/00; C07H 21/02; C07H 21/04; C12N 1/20; C12N 15/11
(52) U.S. Cl. .................. 424/184.1; 435/41; 435/69.1; 435/69.3; 435/69.7; 435/70.1; 435/243; 435/252.1; 435/320.1; 435/325; 435/352.3; 536/23.1; 536/23.5; 424/184.1; 424/185.1; 424/190.1; 424/191.1; 424/192.1; 424/234.1; 424/265.1

(58) Field of Search .................. 435/243, 252.1, 435/41, 69.1, 69.3, 69.7, 70.1, 320.1, 325, 352.3; 536/23.1; 424/184.1, 185.1, 190.1, 191.1, 192.1, 206.1, 236.1, 265.1

(56) References Cited

PUBLICATIONS

Ohashi et al 1998 infection and Immunity 1998, 66: 132–139.*

* cited by examiner

*Primary Examiner*—Lynette R. F. Smith
*Assistant Examiner*—Padmavathi Baskar
(74) *Attorney, Agent, or Firm*—Benjamin Aaron Adler

(57) ABSTRACT

The present invention is directed to the cloning, sequencing and expression of homologous immunoreactive 28-kDa protein genes, p28-1, -2, -3, -5, -6, -7, -9, from a polymorphic multiple gene family of *Ehrlichia canis*. Further disclosed is a multigene locus encoding all nine homologous 28-kDa protein genes of *Ehrlichia canis*. Recombinant *Ehrlichia canis* 28-kDa proteins react with convalescent phase antiserum from an *E. canis*-infected dog, and may be useful in the development of vaccines and serodiagnostics that are particularly effective for disease prevention and serodiagnosis.

2 Claims, 20 Drawing Sheets

```
  1 ATTTATTTATTACCAATCTCTATATAATATATTAAATTTCTCTTACAAAAATCTCTAATG    60
 61 TTTTATACCTATATATATATATTCTGGCTTGTATCTACTTTGCACTTCCACTTATTGTTAAT  120
121 TTATTTTCACTATTTTAGGTGTAATATGTAATTGCAAAAAAATTCTTATAACAACTGCATT   180
                                M  N  C  K  K  I  L  I  T  T  A  L

181 AATATCATTAATGTACTCCTATTCCAAGCATATCTTTTTCTGATACTATACAAGATGGTAA  240
      I  S  L  M  Y  S  I  P  S  I  S  F  S  D  T  I  Q  D  G  N

241 CATGGGTGTAACTTCTCTATATTAGTGGAAAGTATGTACCAAGTGTCTCACATTTGGTAG   300
      M  G  G  N  F  Y  I  S  G  K  Y  V  P  S  V  S  H  F  G  S

301 CTTCTCAGCTAAAGAAGAAAGCAAATCAACTGTTGGAGTTTTTGGATTAAAACATGATTG   360
      F  S  A  K  E  E  S  K  S  T  V  G  V  F  G  L  K  H  D  W

361 GGATGGAAGTCCAATACCTAAGAATAAACGCTGACTTTACTGTTCCAAACTATTCGTT     420
      D  G  S  P  I  L  K  N  K  H  A  D  F  T  V  P  N  Y  S  F

421 CAGATACGAGAACAATCCATTTCTAGGGTTTGCAGGAGCTATCGGTTACTCAATGGGTGG   480
      R  Y  E  N  N  P  F  L  G  F  A  G  A  I  G  Y  S  M  G  G

481 CCCAAGAATAGAATTCGAAATATCTTATGAAGCATTCGACGTAAAAAGTCCTAATATCAA   540
      P  R  I  E  F  E  I  S  Y  E  A  F  D  V  K  S  P  N  I  N

541 TTATCAAAATGACGGCACAGTTACTGTCTTCTTAAAAAACGAAGGGTTAATTGACATATCACTTGCAATAAA  600
      Y  Q  N  D  A  H  R  Y  C  A  L  S  H  H  T  S  A  A  M  E

601 AGCTGATAAATTTGTCTTCTTAAAAAACGAAGGGTTAATTGACATATCACTTGCAATAAA  660
      A  D  K  F  V  F  L  K  N  E  G  L  I  D  I  S  L  A  I  N

661 TGCCATGTTATGATAATAAATGACAAAGTACCTGTTTCTCCTTATATATGCCAGGTAT     720
      A  C  Y  D  I  I  N  D  K  V  P  V  S  P  Y  I  C  A  G  I
```

Fig. 1A

```
721  TGGTACTGATTTGATTTCTATGTTTGAAGCTACAAGTCCTAAAATTTCCTACCAAGGAAA  780
      G  T  D  L  I  S  M  F  E  A  T  S  P  K  I  S  Y  Q  G  K

841  CAGGATCATAGGTAATGAGTTTAGAGAGATATTCCTGCAATAGTACCTAGTAACTCAACTAC  900
      R  I  I  G  N  E  F  R  D  I  P  A  I  V  P  S  N  S  T  T

901  AATAAGTGGACCACAATTTGCAACAGTAACACTAAATGTGTGTCACTTTGGTTTAGAACT  960
      I  S  G  P  Q  F  A  T  V  T  L  N  V  C  H  F  G  L  E  L

961  TGGAGGAAGATTTAACTTCTAATTTTATTGTTGCCACATATTAAAAATGATCTAAACTTG  1020
      G  G  R  F  N  F  (SEQ. ID NO: 2)

1021 TTTTAWTATTGCTACATACAAAAAAAGAAAATAGTGGCAAAAGAATGTAGCAATAAGA    1080
1081 GGGGGGGGGACCAAATTTATCTTCTATGCTTCCCAAGTTTTTCYCGCTATTTATGA      1140
1141 CTTAAACAACAGAAGGTAATATATTTAAATTTCTTCTGCAAAACTTATCTTCAAATATATTTATTATTA 1200
1201 CCAATCTTATATATAATATATATTTCTTGCTTTTCTTCTGCACTTCTACTATTTTAATTTATTTGTCACTAT 1260
1261 TATATATTCTGACTTGCTATAATAAWATGAATTGCMAAAGATTTTTCATAGCAAGTGCATTGATATCACTAA 1320
1321 TAGGTTATATAATAAWATGAATTGCMAAAGATTTTTCATAGCAAGTGCATTGATATCACTAA 1380
1381 TGTCTTTCTTACCTAGCGTATCTTTTTCTGAATCAATACATGAAGATAATATAAATGGTA  1440
1441 ACTTTTACATTAGTGCAAAGTATATGCCAAGTTTCGAGTTTTGGCGTATTTCAGTTA     1500
1501 AAGAAGAGAAAAACACAACAACTGGAGTTTCGGATTAAAACAAGATTGGGACGGAGCAA   1560
1561 CACTAAAGGATGCAAGCWGCCAGCCACACAWTAGACCCAAGTACAATG              1607

(SEQ ID NO: 1)
```

Fig. 1B

```
ECaP28     MNCKKILITTALISLMYSIPSISFSDTIQDGNMG-GN------FYISGKYVPSVSHFGSFSAKE------ESKSTVGVFGLKH    70
ECa28SA2   .....VFTIS....SI.FL.NV.Y.NPVYGNS.-Y..------..........M..P...I...E.------.K.K.TV.Y...E    70
ECa28SA1   .KY..TFTV...VL.TSFTHF.P.YSPARASTIH--------..........M.TA....I.......------.QSF.KVLV..DQ    69
EChP28     ..Y..VF..S.......IS.L.GV....PA-GSGIN-.....----.........M..A....V......------.RNT.......Q    69
OMP-1B     ..Y..FVSS......SIL.YQ..A.PVTSNDT.INDSREG....V..N..I...RK...E.APINGNTSI.KK......K    80
OMP-1C     ....FF.....ALP.SFL.G.LL.EPV..DSVS-...-----.........M..A....V......------.KNP..ALY...Q    70
OMP-1D     ....FF.....TL..SFL.G..L..PV..D.IS-...-----.........M..A....V......------.RNT.......IEQ   70
OMP-1E     ....FF....V....SFL.G.....PV.GD.IS-...-----........V.M.....................-----.KNP..ALY...Q    70
OMP-1F     ....FF...T.V...SFL.G.....AV.ND.V.-..------.........V..M......------....Q------.RNT.T.....Q    70
MAP-1      .........F..ST...VSFL.GV....V..EE.NPV.S-----V...A..M.TA....KM.I......----D.RD.KA.....K   71
                                               →        VR1

ECaP28     DWDGSPILKNKHAD--FTVPNYSFRYENNPFLGFAGAIGYSMGGPRIEFEISYEAFDVKSPNINYQNDAH--RYCALSH--           145
ECa28SA2   N.A.DA.SSQSPD.N..IR....K.AS.K......V.....I.S....V.M......NQGN.    (SEQ ID NO: 7)           133
ECa28SA1   RLSHNI.NN.DT.KSLK.Q....K.K..................I.NS....L.V.H.I..T.N.GN...L..S.--K......GS     147
EChP28     N....A.SNSSPN.V...S....K..................D....L.V...T....NQGN..K.E..------............    145
OMP-1B     ------GDIAQSAN.NRTDPALEFQ..LIS..S.S...A.D....L.AA.QK..A.N..DN.DT.SGDYYK.FG..RED            154
OMP-1C     ..N.-VSASSHADAD.NNKG....K...................V...T....NQGG..K....------..........DR--      145
OMP-1D     ...RCV.SRTTLS.I......K....L.S..........D....L.V.....T....NQGN..K.E..------...Y......      146
OMP-1E     ..E.-ISSSSHNDNH.NNKG....K................V...V...T....NQGN..K......------.........GQ--    145
OMP-1F     ....T.S..SPENT.N......K..................V.L.M....T....NQGN..K......------.K.Y..T.--      146
MAP-1      ...VKTPSGNTNSI..EKD....K...................V......V...T....RN.GG..K......------...M...----   145
               VR2
```

Eca28SA2

```
ATGAATTGTAAAAAAGTTTTCACAATAAGTGCATTGATATCATCCATATACTTCCTACCT    60
 M  N  C  K  K  V  F  T  I  S  A  L  I  S  S  I  Y  F  L  P

AATGTCTCATACTCTAACCCAGTATATGGTAACAGTATGTATGGTAATTTTACATATCA   120
 N  V  S  Y  S  N  P  V  Y  G  N  S  M  Y  G  N  F  Y  I  S

GGAAAGTACATGCCAAGTGTTCCTCATTTTGGAATTTTTTCAGCTGAAGAAGAGAAAAAA   180
 G  K  Y  M  P  S  V  P  H  F  G  I  F  S  A  E  E  E  K  K

AAGACAACTGTAGTATATGGCTTAAAAGAAAATTGGGCAGGAGATGCAATATCTAGTCAA   240
 K  T  T  V  V  Y  G  L  K  E  N  W  A  G  D  A  I  S  S  Q

AGTCCAGATGATAATTTTACCATTCGAAATTACTCATTCAAGTATGCAAGCAACAAGTTT   300
 S  P  D  D  N  F  T  I  R  N  Y  S  F  K  Y  A  S  N  K  F

TTAGGGTTTGCAGTAGCTATTGGTTACTCGATAGGCAGTCCAAGAATAGAAGTTGAGATG   360
 L  G  F  A  V  A  I  G  Y  S  I  G  S  P  R  I  E  V  E  M

TCTTATGAAGCATTTGATGTGAAAAATCCAGGTGATAATTACAAAAACGGTGCTTACAGG   420
 S  Y  E  A  F  D  V  K  N  P  G  D  N  Y  K  N  G  A  Y  R

TATTGTGCTTTATCTCATCAAGATGATGCGGATGATGACATGACTAGTGCAACTGACAAA   480
 Y  C  A  L  S  H  Q  D  D  A  D  D  D  M  T  S  A  T  D  K

TTTGTATATTTAATTAATGAAGGATTACTTAACATATCATTTATGACAAACATATGTTAT   540
 F  V  Y  L  I  N  E  G  L  L  N  I  S  F  M  T  N  I  C  Y

GAAACAGCAAGCAAAAATATACCTCTCTCCCTTACATATGTGCAGGTATTGGTACTGAT   600
 E  T  A  S  K  N  I  P  L  S  P  Y  I  C  A  G  I  G  T  D

TTAATTCACATGTTTGAAACTACACATCCTAAAATTTCTTATCAAGGAAAGCTAGGGTTG   660
 L  I  H  M  F  E  T  T  H  P  K  I  S  Y  Q  G  K  L  G  L
```

Fig. 7A

```
GCCTACTTCGTAAGTGCAGAGTCTTCGGTTTCTCTTTTGGTATATATTTTCATAAAATTATA   720
 A  Y  F  V  S  A  E  S  S  V  S  F  G  I  Y  F  H  K  I  I

AATATAAGTTTAAAAATGTTCCAGCCATGGTTAACTCAGACGAGATAGTAGGA            780
 N  N  K  F  K  N  V  P  A  M  V  P  I  N  S  D  E  I  V  G

CCACAGTTTGCAACAGTAACATTAAATGTATGCTACTTTGGATTAGAACTTGGATGTAGG    840
 P  Q  F  A  T  V  T  L  N  V  C  Y  F  G  L  E  L  G  C  R
                            (SEQ ID NO: 3)

TTCAACTTCTAATTCGTGGTACACATATCACGAAGCTAAAATTGTTTTTTTATCTCTGC     900
 F  N  F  *  (SEQ ID NO: 4)

TGTATACAAGAGAAAAAATAGTAGTGAAAATTACCTAACAATATGACAGTACAAGTTAC     960
CAAGCTTATTCTCACAAAACTTCTTGTGTTCTTTATCTCTTTACAATGTCTTTACACTT    1020
AGCTTCACTACTGTAGAGTGTGTTTATCAATGCTTGTTTATTAATACTCTACATAATAT    1080
GTTAAATTTTCTTACAAAACTCACTAGTAATTATACTAGAATATATATTCTGACTTGT    1140
                                              (SEQ ID NO: 31)

ECa28SA3
ATTTGCTTTATACTTCCACTATTGTAATTTATTTTCACTATTTTAGGTGTAATATGAAT    1200
                                                       M  N

TGCAAAAAATTCTTATAACAACTGCATTAATGTCATTAATGTACTATGCTCCAAGCATA    1260
 C  K  K  I  L  I  T  T  A  L  M  S  L  M  Y  Y  A  P  S  I

TCTTTTTCTGATACTATACAGACGATAACACTGGTAGCTTCTACACATCAGTGGAAAATAT  1320
 S  F  S  D  T  I  Q  D  D  N  T  G  S  F  Y  I  S  G  K  Y

GTACCAAGTGTTCACATTTGGTGTTTTCTCAGCTAAAGAAGAAAGAAACTCAACTGTT    1380
 V  P  S  V  S  H  F  G  V  F  S  A  K  E  E  R  N  S  T  V

GGGAGTTTTTGGATTAAAACATGATTGGAATGGAGGTACAATATCTAACTCTTCTCCAGAA   1440
 G  V  F  G  L  K  H  D  W  N  G  G  T  I  S  N  S  S  P  E
```

Fig. 7B

```
AATATATTCACAGTTCAAAATTATTCGTTTAAATACGAAAACAACCCATTCTTAGGGTTT  1500
 N  I  F  T  V  Q  N  Y  S  F  K  Y  E  N  N  P  F  L  G  F

GCAGGAGCTATTGGTTATTCAATGGGTGGCCCAAGAATAGAACTTGAAGTTCTGTACGAG  1560
 A  G  A  I  G  Y  S  M  G  G  P  R  I  E  L  E  V  L  Y  E

ACATTCGATGTGAAAAATCAGAACAATAATTATAAGAACGGCGCACACAGATACTGTGCT  1620
 T  F  D  V  K  N  Q  N  N  N  Y  K  N  G  A  H  R  Y  C  A

TTATCTCATCATAGTTCAGCAACATGTCCTCCGCAAGTAACAAATTTGTTTTCTTA  1680
 L  S  H  H  S  S  A  T  S  M  S  S  A  S  N  K  F  V  F  L

AAAAATGAAGGGTTAATTGACTTATCATTTATGATAAATGCATGCTATGACATAATAATT  1740
 K  N  E  G  L  I  D  L  S  F  M  I  N  A  C  Y  D  I  I  I

GAAGGAATGCCTTTTTCACCTTATATTTGTGCAGGTGTTGGTACTGATGTTGTTTCCATG  1800
 E  G  M  P  F  S  P  Y  I  C  A  G  V  G  T  D  V  V  S  M

TTTGAAGCTATAAATCCTAAAATTTCTTACCAAGGAAAACTAGGATTAGGTTATAGTATA  1860
 F  E  A  I  N  P  K  I  S  Y  Q  G  K  L  G  L  G  Y  S  I

AGTTCAGAAGCCTCTGTTTTTATCGGTGGACACTTCACAGAGTCATAGGTAATGAATTT  1920
 S  S  E  A  S  V  F  I  G  G  H  F  H  R  V  I  G  N  E  F

AGAGACATCCCTGCTATGGTTCCTAGTGGATCAAATCTTCCAGAAAACCAATTTGCAATA  1980
 R  D  I  P  A  M  V  P  S  G  S  N  L  P  E  N  Q  F  A  I
                                                (SEQ ID NO: 5)
GTAACACTAAATGTGTGTCACTTTGGCATAGAACTTGGAGGAAGATTTAACTTCTGA    2031
 V  T  L  N  V  C  H  F  G  I  E  L  G  G  R  F  N  F  *
                                                (SEQ ID NO: 6)
```

Fig. 7C

```
TAATACTTCTATTGT-ACATGTTAAAAATAGTACTAGTTTGCTTCTGTGGTT--TATAAACGCAAGAGAGAA--  28nc1
...TTCGTGG.A---C....A.C.CG..-GC..AA.T.G.TT..T.A.CTC.GC.G..T..AAG...A.A..TA  28nc2
.G..TT.AT.G...CC....A........GA.CTA.AC...T..T.A.TA..GC..C.T..AA..A.A...AA  28nc3
...TT.AT.G...CC....A........GA.CTA.AC...T..T.AWTA..GC..C.T..AA..A.A--..AA  28nc4

ATAGT-------------TAGTAATAAATTAGAAAG-------TTAAA--TATT---AGAAAAGT-CA       28nc1
G....G--AAAATTACC..AC.....TGAC..T.CAAGTTTACC..GCT....CTC.C....C.T.T        28nc2
.....GGCAAAAGAATG...C......GAGG.GGG.GGGGGAC....TT...CCTTC---T.TTC.T.T      28nc3
.....GGCAAAAGAATG...C......GAGG.GGG.GGGGGACC...TT...CCTTC---T.TGC.T.C      28nc4

TATGTTTTTCATTGTCATTGAT-ACTCAACTA-----AAAGTAGTAT-------AAATGT-------------  28nc1
.G..C...T..CTCT---.T.CA.-.G..A.-GTAC.-CT..CT.CACTACTGTAG.G...GTTATCAATGC   28nc2
A..A..C..T---ACT..-----T...A.GCAC..CTC.A.GCTTCCA-GG-A...A.GT-TTCTAAATAT    28nc3
C.A......TCYC.CT...T..G...T.AC.ACAG..G..A...CCTCACGG-A....CT.ATCTTCAAATAT  28nc4

--TACTTATTAATAAT-TTTACGTAGTATATTAAATTCCCTTACAAAAGCCACTAGTATTTTATA          28nc1
TT.GT........-.C.C...A..A...G........TT......CT....A........              28nc2
TT..T.......CC....CC...TA..A..............T.....AT.T...A.G........        28nc3
TT..T.......CC...C-...TA..A..............T.....AT................         28nc4
                                        -10

CTAAAAGC-TATACTTTGGCTTGTATTTAATTTGTATTTTACTACTGTTAATTTACTT--TCACTGTT---TCT 28nc1
-T.G.ATA...T.C.A.........GC..A..C.CC....T..............T-..---.A.---..TA  28nc2
..T..TATA...T.C..................C...CC...T..............T.......A.....TA 28nc3
.C-...ATA....T.C.A.....CT....CT..C.C.C..C.....T.T_____T..G....A.AGG.TA 28nc4
                    -35                              -10

GGTGTAAAT  28nc1  (SEQ ID NO: 30)
.........  28nc2  (SEQ ID NO: 31)
.........  28nc3  (SEQ ID NO: 32)
TA-A...-W  28nc4  (SEQ ID NO: 33)
   RBS
```

Fig. 10

```
ATGAATAATAAACTCAAATTTACTATAATAAACACAGTATTAGTATGCTTATTGTCATTA  60
 M   N   N   K   L   F   T   I   I   N   T   V   L   V   C   L   L   S   L

CCTAATATATCTTCCTCAAAGGCCATAAACAATAACGCTAAAAAGTACTACGGATTATAT  120
 P   N   I   S   S   S   K   A   I   N   N   N   A   K   K   Y   Y   G   L   Y

ATCAGTGGACAATATAAACCCAGTGTTTCTGTTTTCAGTAATTTTTCAGTTAAAGAAACC  180
 I   S   G   Q   Y   K   P   S   V   S   V   F   S   N   F   S   V   K   E   T

AATGTCATAACTAAAAACCTTATAGCTTTAAAAAAAGATGTTGACTCTATTGAAACCAAG  240
 N   V   I   T   K   N   L   I   A   L   K   K   D   V   D   S   I   E   T   K

ACTGATGCCAGTGTAGGTATTAGTAACCCATCAAATTTTACTATCCCCTATACAGCTGTA  300
 T   D   A   S   V   G   I   S   N   P   S   N   F   T   I   P   Y   T   A   V

TTTCAAGATAATTCTGTCAATTTCAATGGAACTATTGGTTACACCTTTGCTGAAGGTACA  360
 F   Q   D   N   S   V   N   F   N   G   T   I   G   Y   T   F   A   E   G   T

AGAGTTGAAATAGAAGGTTCTTATGAGGAATTTGATGTTAAAAACCCTGGAGGCTATACA  420
 R   V   E   I   E   G   S   Y   E   E   F   D   V   K   N   P   G   G   Y   T

CTAAGTGATGCCTATCGCTATTTTGCATTAGCACGTGAAATGAAAGGTAATAGTTTTACA  480
 L   S   D   A   Y   R   Y   F   A   L   A   R   E   M   K   G   N   S   F   T

CCTAAAGAAAAAGTTTCTAATAGTATTTTTCACACTGTAATGAGAAATGATGGATTATCT  540
 P   K   E   K   V   S   N   S   I   F   H   T   V   M   R   N   D   G   L   S

ATAATATCTGTTATAGTAAATGTTTGCTACGATTTCTCTTTGAACAATTTGTCAATATCG  600
 I   I   S   V   I   V   N   V   C   Y   D   F   S   L   N   N   L   S   I   S

CCTTACATATGTGGAGGAGCAGGGGTAGATGCTATAGAATTCTTCGATGTATTACACATT  660
 P   Y   I   C   G   G   A   G   V   D   A   I   E   F   F   D   V   L   H   I

AAGTTTGCATATCAAAGCAAGCTAGGTATTGCTTATTCTCTACCATCTAACATTAGTCTC  720
 K   F   A   Y   Q   S   K   L   G   I   A   Y   S   L   P   S   N   I   S   L

TTTGCTAGTTTATATTACCATAAAGTAATGGGCAATCAATTTAAAAATTTAAATGTCCAA  780
 F   A   S   L   Y   Y   H   K   V   M   G   N   Q   F   K   N   L   N   V   Q

CATGTTGCTGAACTTGCAAGTATACCTAAAATTACATCCGCAGTTGCTACACTTAATATT  840
 H   V   A   E   L   A   S   I   P   K   I   T   S   A   V   A   T   L   N   I

GGTTATTTTGGAGGTGAAATTGGTGCAAGATTGACATTT   (SEQ ID No. 39)      879
 G   Y   F   G   G   E   I   G   A   R   L   T   F   (SEQ ID NO. 40)
```

Fig. 13

```
ATGAATTATAAGAAAATTCTAGTAAGAAGCGCGTTAATCTCATTAATGTCAATCTTACCA  60
 M  N  Y  K  K  I  L  V  R  S  A  L  I  S  L  M  S  I  L  P
TATCAGTCTTTTGCAGATCCTGTAGGTTCAAGAACTAATGATAACAAAGAAGGCTTCTAC 120
 Y  Q  S  F  A  D  P  V  G  S  R  T  N  D  N  K  E  G  F  Y
ATTAGTGCAAAGTACAATCCAAGTATATCACACTTTAGAAAATTCTCTGCTGAAGAAACT 180
 I  S  A  K  Y  N  P  S  I  S  H  F  R  K  F  S  A  E  E  T
CCTATTAATGGAACAAATTCTCTCACTAAAAAAGTTTTCGGACTAAAGAAAGATGGTGAT 240
 P  I  N  G  T  N  S  L  T  K  K  V  F  G  L  K  K  D  G  D
ATAACAAAAAAGACGATTTTACAAGAGTAGCTCCAGGCATTGATTTTCAAAATAACTTA 300
 I  T  K  K  D  D  F  T  R  V  A  P  G  I  D  F  Q  N  N  L
ATATCAGGATTTTCAGGAAGTATTGGTTACTCTATGGACGGACCAAGAATAGAACTTGAA 360
 I  S  G  F  S  G  S  I  G  Y  S  M  D  G  P  R  I  E  L  E
GCTGCATATCAACAATTTAATCCAAAAAACACCGATAACAATGATACTGATAATGGTGAA 420
 A  A  Y  Q  Q  F  N  P  K  N  T  D  N  N  D  T  D  N  G  E
TACTATAAACATTTTGCATTATCTCGTAAAGATGCAATGGAAGATCAGCAATATGTAGTA 480
 Y  Y  K  H  F  A  L  S  R  K  D  A  M  E  D  Q  Q  Y  V  V
CTTAAAAATGACGGCATAACTTTTATGTCATTGATGGTTAATACTTGCTATGACATTACA 540
 L  K  N  D  G  I  T  F  M  S  L  M  V  N  T  C  Y  D  I  T
GCTGAAGGAGTATCTTTCGTACCATATGCATGTGCAGGTATAGGAGCAGATCTTATCACT 600
 A  E  G  V  S  F  V  P  Y  A  C  A  G  I  G  A  D  L  I  T
ATTTTTAAAGACCTCAATCTAAAATTTGCTTACCAAGGAAAAATAGGTATTAGTTACCCT 660
 I  F  K  D  L  N  L  K  F  A  Y  Q  G  K  I  G  I  S  Y  P
ATCACACCAGAAGTCTCTGCATTTATTGGTGGATACTACCATGGCGTTATTGGTAATAAA 720
 I  T  P  E  V  S  A  F  I  G  G  Y  Y  H  G  V  I  G  N  K
TTTGAGAAGATACCTGTAATAACTCCTGTAGTATTAAATGATGCTCCTCAAACCACATCT 780
 F  E  K  I  P  V  I  T  P  V  V  L  N  D  A  P  Q  T  T  S
GCTTCAGTAACTCTTGACGTTGGATACTTTGGCGGAGAAATTGGAATGAGGTTCACCTTC 840
                                                   (SEQ ID No. 41)
 A  S  V  T  L  D  V  G  Y  F  G  G  E  I  G  M  R  F  T  F
                                                   (SEQ ID No. 42)
```

Fig. 14

```
ATGAACTGTAAAAAAATTCTTATAACAACTACATTGGTATCACTAACAATTCTTTTACCT  60
 M  N  C  K  K  I  L  I  T  T  T  L  V  S  L  T  I  L  L  P
GGCATATCTTTCTCCAAACCAATACATGAAAACAATACTACAGGAAACTTTTACATTATT 120
 G  I  S  F  S  K  P  I  H  E  N  N  T  T  G  N  F  Y  I  I
GGAAAATATGTACCAAGTATTTCACATTTTGGAACTTTTCAGCTAAAGAAGAAAAAAAC  180
 G  K  Y  V  P  S  I  S  H  F  G  N  F  S  A  K  E  E  K  N
ACAACAACTGGAATTTTTGGATTAAAAGAATCATGGACTGGTGGTATCATCCTTGATAAA 240
 T  T  T  G  I  F  G  L  K  E  S  W  T  G  G  I  I  L  D  K
GAACATGCAGCTTTTAATATCCCAAATTATTCATTTAAATATGAAAATAATCCATTTTTA 300
 E  H  A  A  F  N  I  P  N  Y  S  F  K  Y  E  N  N  P  F  L
GGATTTGCAGGGGTAATTGGCTATTCAATAGGTAGTCCAAGAATAGAATTTGAAGTATCA 360
 G  F  A  G  V  I  G  Y  S  I  G  S  P  R  I  E  F  E  V  S
TACGAGACATTCGATGTACAAAATCCAGGAGATAAGTTTAACAATGATGCACATAAGTAT 420
 Y  E  T  F  D  V  Q  N  P  G  D  K  F  N  N  D  A  H  K  Y
TGTGCTTTATCCAATGATTCCAGTAAAACAATGAAAAGTGGTAAATTCGTTTTTCTCAAA 480
 C  A  L  S  N  D  S  S  K  T  M  K  S  G  K  F  V  F  L  K
AATGAAGGATTAAGTGACATATCACTCATGTTAAATGTATGTTATGATATAATAAACAAA 540
 N  E  G  L  S  D  I  S  L  M  L  N  V  C  Y  D  I  I  N  K
AGAATGCCTTTTTCACCTTACATATGTGCAGGCATTGGTACTGACTTAATATTCATGTTT 600
 R  M  P  F  S  P  Y  I  C  A  G  I  G  T  D  L  I  F  M  F
GACGCTATAAACCATAAAGCTGCTTATCAAGGAAAATTAGGTTTTAATTATCCAATAAGC 660
 D  A  I  N  H  K  A  A  Y  Q  G  K  L  G  F  N  Y  P  I  S
CCAGAAGCTAACATTTCTATGGGTGTGCACTTTCACAAAGTAACAAACAACGAGTTTAGA 720
 P  E  A  N  I  S  M  G  V  H  F  H  K  V  T  N  N  E  F  R
GTTCCTGTTCTATTAACTGCTGGAGGACTCGCTCCAGATAATCTATTTGCAATAGTAAAG 780
 V  P  V  L  L  T  A  G  G  L  A  P  D  N  L  F  A  I  V  K
TTGAGTATATGTCATTTTGGGTTAGAATTTGGGTACAGGGTCAGTTTT(SEQ ID No. 43)828
 L  S  I  C  H  F  G  L  E  F  G  Y  R  V  S  F  (SEQ ID NO. 44)
```

Fig. 15

```
ATGAATTACAAAAGATTTGTTGTAGGTGTTACGCTGAGTACATTTGTTTTTTTCTTATCT  60
 M  N  Y  K  R  F  V  V  G  V  T  L  S  T  F  V  F  F  L  S

GATGGTGCTTTTTCTGATGCAAATTTTTCTGAAGGGAGGAGAGGACTTTATATAGGTAGT 120
 D  G  A  F  S  D  A  N  F  S  E  G  R  R  G  L  Y  I  G  S

CAGTATAAAGTTGGTATTCCCAATTTTAGTAATTTTTCAGCTGAAGAAACAATTCCTGGT 180
 Q  Y  K  V  G  I  P  N  F  S  N  F  S  A  E  E  T  I  P  G

ATTACAAAAAAGATTTTTGCGTTAGGTCTTGATAAGTCTGAGATAAATACTCACAGCAAT 240
 I  T  K  K  I  F  A  L  G  L  D  K  S  E  I  N  T  H  S  N

TTTACACGATCATATGACCCTACTTATGCAAGCAGTTTTGCAGGGTTTAGTGGTATCATT 300
 F  T  R  S  Y  D  P  T  Y  A  S  S  F  A  G  F  S  G  I  I

GGATATTATGTTAATGACTTTAGGGTAGAATTTGAAGGTTCTTATGAGAATTTTGAACCT 360
 G  Y  Y  V  N  D  F  R  V  E  F  E  G  S  Y  E  N  F  E  P

GAAAGACAATGGTACCCTGAGAATAGCCAAAGCTACAAATTTTTTGCTTTGTCTCGAAAT 420
 E  R  Q  W  Y  P  E  N  S  Q  S  Y  K  F  F  A  L  S  R  N

GCTACAAATAGTGATAATAAGTTTATAGTACTAGAGAATAACGGCGTTGTTGACAAGTCT 480
 A  T  N  S  D  N  K  F  I  V  L  E  N  N  G  V  V  D  K  S

CTTAATGTAAATGTTTGTTATGATATTGCTAGTGGTAGTATTCCTTTAGCACCTTATATG 540
 L  N  V  N  V  C  Y  D  I  A  S  G  S  I  P  L  A  P  Y  M

TGTGCTGGTGTTGGTGCAGATTATATAAAGTTTTTAGGTATATCATTGCCTAAGTTTTCT 600
 C  A  G  V  G  A  D  Y  I  K  F  L  G  I  S  L  P  K  F  S

TATCAAGTTAAGTTTGGTGTCAACTACCCTCTAAATGTTAATACTATGTTGTTTGGTGGG 660
 Y  Q  V  K  F  G  V  N  Y  P  L  N  V  N  T  M  L  F  G  G

GGTTATTACCATAAGGTTGTAGGTGATAGGCATGAGAGAGTAGAAATAGCTTACCATCCT 720
 G  Y  Y  H  K  V  V  G  D  R  H  E  R  V  E  I  A  Y  H  P

ACTGCATTATCTGACGTTCCTAGAACTACTTCAGCTTCTGCTACTTTAAATACTGATTAT 780
 T  A  L  S  D  V  P  R  T  T  S  A  S  A  T  L  N  T  D  Y

TTTGGTTGGGAGATTGGATTTAGATTTGCGCTA (SEQ ID No. 45)            813
 F  G  W  E  I  G  F  R  F  A  L  (SEQ ID No. 46)
```

Fig. 16

HOMOLOGOUS 28-KILODALTON IMMUNODOMINANT PROTEIN GENES OF *EHRLICHIA CANIS* AND USES THEREOF

CROSS-REFERENCE TO RELATED APPLICATION

This patent application is a divisional application Ser. No. 09/660,587 filed Sep. 12, 2000 of U.S. Pat. No. 6,392,023, which is a continuation-in-part Ser. No. 09/261,358, Mar. 3, 1999 of U.S. Pat. No. 6,403,780, which is a continuation-in-part Ser. No. 09/201,458, Nov. 30, 1998 of U.S. Pat. No. 6,458,942.

BACKGROUND OF THE INVENTION

1. Field of the Invention

The present invention relates generally to the field of molecular biology. More specifically, the present invention relates to molecular cloning and characterization of homologous 28-kDa protein genes in *Ehrlichia canis*, a multigene locus encoding the 28-kDa homologous proteins of *Ehrlichia canis* and uses thereof.

2. Description of the Related Art

Canine ehrlichiosis, also known as canine tropical pancytopenia, is a tick-borne rickettsial disease of dogs first described in Africa in 1935 and the United States in 1963 (Donatien and Lestoquard. 1935; Ewing, 1963). The disease became better recognized after an epizootic outbreak occurred in United States military dogs during the Vietnam War (Walker et al., 1970)

The etiologic agent of canine ehrilichiosis is *Ehrlichia canis*, a small, gram-negative, obligate intracellular bacterium which exhibits tropism for mononuclear phagocytes (Nyindo et al., 1971) and is transmitted by the brown dog tick, *Rhipicephalus sanguineus* (Groves et al., 1975). The progression of canine ehrlichiosis occurs in three phases, acute, subclincal and chronic. The acute phase is characterized by fever, anorexia, depression, lymphadenopathy and mild thrombocytopenlia (Troy and Forrester, 1990). Dogs typically recover from the acute phase, but become persistently infected carriers of the organism without clinical signs of disease for months or even years (Harrus et al., 1998). A chronic phase develops in some cases that is characterized by thrombocytopenia, hyperglobulinemia, anorexia, emaciation, and hemorrhage, particularly epistaxis, followed by death (Troy and Forrester, 1990).

Regulation of surface antigenicity may be an important mechanism for the establishment of such persistent infections in the host. Although disease pathogenesis is poorly understood, multigene families described in members of the related genera Ehrlichia, Anaplamsa, and Cowdria may be involved in variation of major surface antigen expression thereby evading immune surveillance. *Anaplasma marginale*, an organism closely related to *E. canis*, exhibits variation of major surface protein 3 (msp-3) genes resulting in antigenic polymorphism among strains (Alleman et al., 1997).

Molecular taxonomic analysis based on the 16S rRNA gene has determined that *E. canis* and *E. chaffeensis*, the etiologic agent of human nionocytic ehrlichiosis (HME), are closely related (Anderson et al., 1991; Anderson et al., 1992: Dawson et al., 1991; Chen et al., 1994). Considerable cross reactivity of the 64, 47, 40, 30, 29 and 23-kDa antigens between *E. canis* and *E. chaffeensis* has been reported (Chen et al., 1994; Chen et al., 1997; Rikihisa et al., 1994; Rikihisa et al., 1992). Analysis of immunoreactive antigens with human and canine convalescent phase sera by immunoblot has resulted in the identification of numerous immunodominant proteins of *E. canis*, including a 30-kDa protein (Chen et al., 1997). In addition, a 30-kDa protein of *E. canis* has been described as a major immunodominant antigen recognized early in the immune response that is antigenically distinct from the 30-kDa protein of *E. chaffeensis* (Rikihisa et al., 1992; Rikihisa et al., 1994). Other immunodominant proteins of *E. canis* with molecular masses ranging from 20 to 30-kDa have also been identified (Brouqui et al., 1992; Nyindo et al. 1991; Chen et al., 1994; Chen et al., 1997).

Homologous 28–32 kDa immunodominant proteins encoded by multigene families have been reported in related organisms including, *E. chaffeensis* and *Cowdria ruminantium* (Sulsona et al., 1999; Ohashi et al., 1998a; Reddy et al., 1998). Recently, characterization of a 21 member multigene family encoding proteins of 23 to 28-kDa has been described in *E. chaffeensis* (Yu et al., 2000). The *E. chaffeensis* 28-kDa outer membrane proteins arc surface exposed, and contain three major hypervariable regions (Ohashi et al., 1998a). The recombinant *E. chaffeensis* P28 appeared to provide protection against homologous challenge infection in mice, and antisera produced against the recombinant protein cross reacted with a 30-kDa protein of *E. canis* (Ohashi et al., 1998a). Diversity in the p28 gene among *E. chaffeensis* isolates has been reported (Yu et al., 1999a), and studies using monoclonal antibodies have further demonstrated diversity in the expressed P28 proteins (Yu et al., 1993). Conversely, complete conservation of a p28 genes in geographically different isolates of *E. canis* has been reported and suggests that *E. canis* may be conserved in North America (McBride et al., 1999, 2000).

The prior art is deficient in the lack of cloning and characterization of new homologous 28-kDa immunoreactive protein genes of *Ehrlichia canis* and a single multigene locus containing the homologous 28-kDa protein genes. Further, The prior art is deficient in the lack of recombinant proteins of such immunoreactive genes of *Ehrlichia canis*. The present invention fulfills this long-standing need and desire in the art.

SUMMARY OF THE INVENTION

Certain embodiments of the present invention describe the molecular cloning, sequencing, characterization, and expression of homologous mature 28-kDa immunoreactive protein genes of *Ehrlichia canis* (designated p28-1, -2, -3, -5, -6, -7, -9), and the identification of a single locus (10,677-bp) containing nine 28-kDa protein genes of *Ehrlichia canis* (p28-1 to p28-9). Eight of the p28 genes were located on one DNA strand, and one p28 gene was found on the complementary strand. The nucleic acid homology among the nine p28 gene members was 37 to 75%, and the amino acid homology ranged from 28 to 72%.

In one embodiment of the present invention, there are provided DNA sequences encoding a 30-kDa immunoreactive protein of *Ehrlichia canis*. Preferably, the protein has an amino acid sequence selected from the group consisting of SEQ ID No. 2, 4, 6, 40, 42, 44, 46 and the gene has a nucleic acid sequence selected from the group consisting of SEQ ID No. 1, 3, 5, 39, 41, 43, 45 and is a member of a polymorphic multiple gene family. Generally, the protein has an N-terminal signal sequence which may be cleaved after post-translational process resulting in the production of a mature 28-kDa protein. Furthermore, the genes encoding 28-kDa proteins are preferably contained in a single multigene locus, which has the size of 10,677 bp and encodes nine homologous 28-kDa proteins of *Ehrlichia canis*.

In another embodiment of the present invention, there is provided an expression vector comprising a gene encoding a 28-kDa immunoreactive protein of Ehrlichia canis and capable of expressing the gene when the vector is introduced into a cell.

In still another embodiment of the present invention, there is provided a recombinant protein comprising an amino acid sequence selected from the group consisting of SEQ ID No. 2, 4, 6, 40, 42, 44, and 46. Preferably, the amino acid sequence is encoded by a nucleic acid sequence selected from the group consisting of SEQ ID No. 1, 3, 5, 39, 41, 43, and 45. Preferably, the recombinant protein comprises four variable regions which may be surface exposed, hydrophilic and antigenic. The recombinant protein may be useful as an antigen.

In yet another embodiment of the present invention, there is provided a method of producing the recombinant protein comprising the steps of obtaining a vector that comprises an expression region comprising a sequence encoding the amino acid sequence selected from the group consisting of SEQ ID No. 2, 4, 6, 40, 42, 44, and 46 operatively linked to a promoter; transfecting the vector into a cell; and culturing the cell under conditions effective for expression of the expression region.

The invention may also be described in certain embodiments as a method of inhibiting Ehrlichia canis infection in a subject comprising the steps of: identifying a subject prior to exposure or suspected of being exposed to or infected with Ehrlichia canis; and administering a composition comprising a 28-kDa antigen of Ehrlichia canis in an amount effective to inhibit an Ehrlichia canis infection. The inhibition may occur through any means such as, e.g., the stimulation of the subject's humoral or cellular immune responses, or by other means such as inhibiting the normal function of the 28-kDa antigen, or even competing with the antigen for interaction with some agent in the subject's body.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows nucleic acid sequence (SEQ ID No. 1) and deduced amino acid sequence (SEQ ID No. 2) of p28-7 gene including adjacent 5' and 3' non-coding sequences. The ATG start codon and TAA termination are shown in bold, and the 23 amino acid leader signal sequence is underlined.

FIG. 3 shows amino acid sequences alignment of p28-7 protein (ECa28-1, SEQ ID NO. 2), p28-5 protein (ECa28SA2, partial sequence, SEQ ID NO. 7), p28-4 protein (ECa28SA1, SEQ ID NO. 8), E. chaffeensis P28 (SEQ ID NO. 9), E. chaffeensis OMP-1 family (SEQ ID NOs: 10–14) and C. ruminantium MAP-1 protein (SEQ ID NO. 15). The p28-7 amino acid sequence is presented as the consensus sequence. Amino acids not shown are identical to p28-7 and are represented by a dot. Divergent amino acids are shown with the corresponding one letter abbreviation. Gaps introduced for maximal alignment of the amino acid sequences are denoted with a dash. Variable regions are underlined and denoted (VR1, VR2, VR3, and VR4). The arrows indicate the predicted signal peptidase cleavage site for the signal peptide.

FIG. 7 shows nucleic acid sequences and deduced amino acid sequences of the E. canis 28-kDa protein genes p28-5 (nucleotide 1–849: SEQ ID No. 3; amino acid sequence: SEQ ID No. 4) and p28-6 (nucleotide 1195–2031: SEQ ID No. 5; amino acid sequence: SEQ ID No. 6) including intergenic noncoding sequences (NC2, nucleotide 850–1194: SEQ ID No. 31). The ATG start codon and termination condons are shown in bold.

FIG. 10 shows alignment of E. canis 28-kDa protein gene intergenic noncoding nucleic acid sequences (SEQ ID Nos.

30–33). Nucleic acids not shown, denoted with a dot (.), are identical to noncoding region 1 (28NC1). Divergence is shown with the corresponding one letter abbreviation. Gaps introduced for maximal alignment of the amino acid sequences are denoted with a dash (–). Putative transcriptional promoter regions (–10 and –35) and ribosomal binding site (RBS) are boxed.

Figure 11:
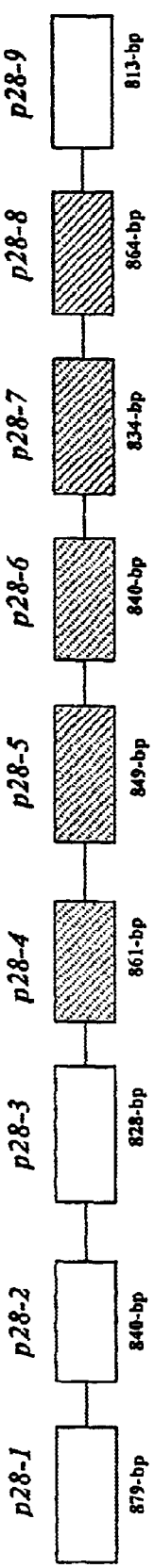

FIG. 11 shows schematic representation of the nine gene *E. canis* p28 locus (10,677-bp) indicating genomic orientation and intergenic noncoding regions. The p28 genes (p28-1, 2, 3, 9) (unshaded) were identified in Example 8. Shaded p28 genes have been identified previously and designated as follows: p28-4, p30a (Ohashi et al., 1998b) and ORF1 (Reddy et al., 1998); p28-5 and p28-6, (McBride, et. al., 2000); p28-7, p28 (McBride et al., 1999) and p30 (Ohashi et al., 1998b); and p28-8, p30-1 (Ohashi et al., 1998b).

Figure 12:
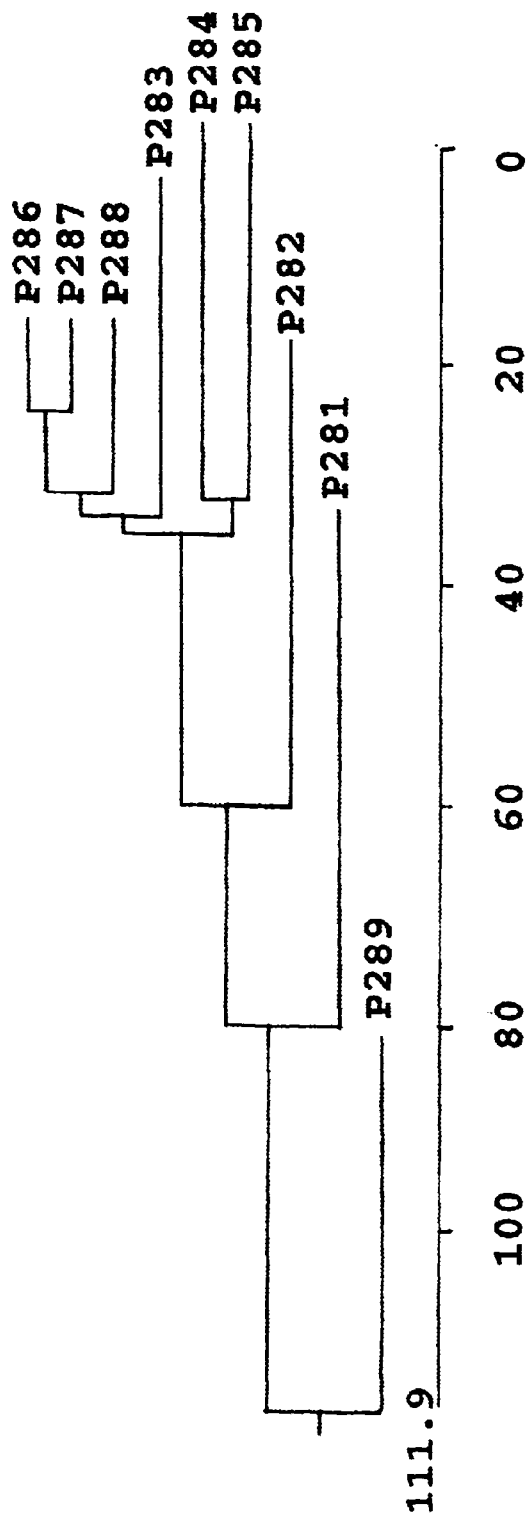

FIG. 12 shows phylogenetic relationships of *E. canis* P28-1 to P28-9 based on the amino acid sequences. The length of each pair of branches represents the distance between amino acid pairs. The scale measures the percentage of divergence between the sequences.

FIG. 13 shows nucleic acid sequence (SEQ ID No. 39) and deduced amino acid sequence (SEQ ID No. 40) of *E. canis* p28-1 gene.

FIG. 14 shows nucleic acid sequence (SEQ ID No. 41) and deduced amino acid sequence (SEQ ID No. 42) of *E. canis* p28-2 gene.

FIG. 15 shows nucleic acid sequence (SEQ ID No. 43) and deduced amino acid sequence (SEQ ID No. 44) of *E. canis* p28-3 gene.

FIG. 16 shows nucleic acid sequence (SEQ ID No. 45) and deduced amino acid sequence (SEQ ID No. 46) of *E. canis* p28-9 gene.

DETAILED DESCRIPTION OF THE INVENTION

The present invention describes cloning, sequencing and expression of homologous genes encoding a 30-kilodalton (kDa) protein of *Ehrlichia canis*. A comparative molecular analysis of homologous genes among seven *E. canis* isolates and the *E. chaffeensis* omp-1 multigene family was also performed. Several new 28-kDa protein genes are identified as follows:

p28-7 (ECa28-1) has an 834-bp open reading frame encoding a protein of 278 amino acids (SEQ ID No. 2) with a predicted molecular mass of 30.5-kDa. An N-terminal signal sequence was identified suggesting that the protein is post-translationally modified to a mature protein of 27.7-kDa.

P28-6 (ECa28SA3) has an 840-bp open reading frame encoding a 280 amino acid protein (SEQ ID No. 6).

Using PCR to amplify 28-kDa protein genes of *E. canis*, a previously unsequenced region of p28-5 (Eca28SA2) was completed. Sequence analysis of p28-5 revealed an 849-bp open reading frame encoding a 283 amino acid protein (SEQ ID No. 4).

PCR amplification using primers specific for 28-kDa protein gene intergenic noncoding regions led to the sequencing of regions linkeking two previously separate loci, thereby identifying a single locus (5.592-kb) containing five 28-kDa protein genes (p28-4, -5, -6, -7 and -8). The five 28-kDa proteins were predicted to have signal peptides resulting in mature proteins, and had amino acid homology ranging from 51 to 72%. Analysis of intergenic regions revealed hypothetical promoter regions for each gene, suggesting that these genes may be independently and differentially expressed. Intergenic noncoding regions (28NC1-4) ranged in size from 299 to 355-bp, and were 48 to 71% homologous.

Furthermore, previously unknown regions of DNA upstream and downstream of the above five gene locus of tandemly arranged p28 genes were sequenced, and p28-1, -2, -3, and -9 were identified. Consequently, a nine gene *E. canis* p28 locus spanning 10, 677 bp was identified in the present invention.

The present invention is directed to, inter alia, homologous 28-kDa protein genes in *Ehrlichia canis*, p28-1, -2, -3, -6, -7, and p28-9, and a complete sequence of previously partially sequenced p28-5. Also disclosed is a multigene locus encoding nine homologous 28-kDa outer membrane proteins of *Ehrlichia canis*. Eight of the p28 genes were located on one DNA strand, and one p28 gene was found on the complementary strand. The nucleic acid homology among the nine p28 gene members was 37 to 75% and the amino acid homology ranged from 28 to 72%.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The invention includes a substantially pure DNA encoding a 28-kDa immunoreactive protein of *Ehrlichia canis*. The protein encoded by the DNA of this invention may share at least 80% sequence identity (preferably 85%, more preferably 90%, and most preferably 95%) with the amino acids listed in SEQ ID No. 2, 4, 6, 40, 42, 44 or 46. More preferably, the DNA includes the coding sequence of the nucleotides of SEQ ID No. 1, 3, 5, 39, 41, 43, 45, or a degenerate variant of such a sequence.

It is well known in the art that the amino acid sequence of a protein is determined by the nucleotide sequence of the DNA that encodes the protein. Because of the degeneracy of the genetic code (i.e., for most amino acids, more than one nucleotide triplet (codon) codes for a single amino acid), different nucleotide sequences can code for a particular amino acid, or polypeptide. Thus, the polynucleotide sequences of the subject invention also encompass those degenerate sequences that encode the polypeptides of the subject invention, or a fragment or variant thereof.

This invention also includes a substantially pure DNA containing a sequence of at least 15 consecutive nucleotides (preferably 20, more preferably 30, even more preferably 50, and most preferably all) of the region from the nucleotides listed in SEQ ID No 1, 3, 5, 39, 41, 43, or 45.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding an additional polypeptide sequence, e.g., a fusion protein. Also included in the present invention is a recombinant DNA which includes a portion of the nucleotides listed in SEQ ID No 1, 3, 5, 39, 41, 43, or 45 which encodes a 28-kDa immunoreactive protein of *Ehrlichia canis*.

The DNA should have at least about 70% sequence identity to the coding sequence of the nucleotides listed in SEQ ID No 1, 3, 5, 39, 41, 43, or 45, preferably at least 75% (e.g. at least 80%); and most preferably at least 90% identity. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The present invention also comprises a vector comprising a DNA sequence coding for a which encodes a gene encoding a 28-kDa immunoreactive protein of *Ehrlichia canis* and said vector is capable of replication in a host which comprises, in operable linkage: a) an origin of replication; b) a promoter; and c) a DNA sequence coding for said protein. Preferably, the vector of the present invention contains a portion of the DNA sequence shown in SEQ ID No 1, 3, 5, 39, 41, 43, or 45.

A "vector" may be defined as a replicable nucleic acid construct, e.g., a plasmid or viral nucleic acid. Vectors may be used to amplify and/or express nucleic acid encoding a 28-kDa immunoreactive protein of *Ehrlichia canis*. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecutlar Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses. adenovirus, adeno-associated virus, SV40 virus, or herpes viruses.

In general, expression vectors containing promoter sequences which facilitate the efficient transcription of the inserted DNA fragment are used in connection with the host. As used herein. the term "host" is meant to include not only prokaryotes but also eukaryotes such as yeast, plant and animal cells. A recombinant DNA molecule or gene which encodes a 28-kDa immunoreactive protein of *Ehrlichia canis* of the present invention can be used to transform a host using any of the techniques commonly known to those of ordinary skill in the art. Especially preferred is the use of a vector containing coding sequences for a gene encoding a 28-kDa immunoreactive protein of *Ehrlichia canis* of the present invention for purposes of prokaryote transformation.

Prokaryotic hosts may include *E. coli, S. tymphimurium, Serratia marcescens* and *Bacillus subtilis*. Eukaryotic hosts include yeasts such as *Pichia pastoris*, mammalian cells and insect cells. The transformed hosts can be fermented and cultured according to means known in the art to achieve optimal cell growth.

As used herein, the term "engineered" or "recombinant" cell is intended to refer to a cell into which a recombinant gene, such as a gene encoding an *Ehrlichia canis* antigen has been introduced. Therefore, engineered cells are distinguishable from naturally occurring cells which do not contain a recombinaintly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene. In addition, the recombinant gene may be integrated into the host genome, or it may be contained in a vector, or in a bacterial genome transfected into the host cell.

The present invention is also drawn to substantially pure 28–30 kDa immunoreactive proteins of *E. canis* comprise of amino acid sequences listed in, for example, SEQ ID No. 2, 4, 6, 40, 42, 44, or 46.

By a "substantially pure protein" is meant a protein which has been separated from at least some of those components which naturally accompany it. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure 28-kDa immunoreactive protein of *Ehrlichia canis* may be obtained, for example, by extraction from a natural source, by expression of a recombinant nucleic acid encoding a 28-kDa immunoreactive protein of *Ehrlichia canis*; or by chemically synthesizing the protein. Purity can be measured by any appropriate method, e.g. column chromatography such as immunoaffinity chromatography using an antibody specific for a 28-kDa immunoreactive protein of *Ehrlichia canis*, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments (e.g., antigenic fragments) of the 28-kDa immunoreactive protein of *Ehrlichia canis* (SEQ ID No. 2, 4, 6, 40, 42, 44, or 46). As used herein, "fragment," as applied to a polypeptide, will ordinarily be at least 10 residues, more typically at least 20 residues and preferably at least 30 (e.g., 50) residues in length, but less than the entire, intact sequence. Fragments of the 28-kDa immunoreactive protein of *Ehrlichia canis* can be generated by methods known to those skilled in the art, e.g., by enzymatic digestion of naturally occurring or recombinant 28-kDa immunoreactive protein of *Ehrlichia canis*, by recombinant DNA techniques using an expression vector that encodes a defined fragment of 28-kDa immunoreactive protein of *Ehrlichia canis*, or by chemical synthesis. The ability of a candidate fragment to exhibit a characteristic of 28-kDa immunoreactive protein of *Ehrlichia canis* (e.g., binding to an antibody specific for 28-kDa immunoreactive protein of *Ehrlichia canis*) can be assessed by methods described herein.

Purified 28-kDa immunoreactive protein of *Ehrlichia canis* or antigenic fragments of 28-kDa immunoreactive protein of *Ehrlichia canis* can be used to generate new antibodies or to test existing antibodies (e.g., as positive controls in a diagnostic assay) by employing standard protocols known to those skilled in the art.

As is well known in the art, a given polypeptide may vary in its immunogenicity. It is often necessary therefore to couple the immunogen (e.g., a polypeptide of the present invention) with a carrier. Exemplary and preferred carriers are keyhole limpet hemocyanin (KLH) and human serum albumin. Means for conjugating a polypeptide to a carrier protein are well known in the art and include glutaraldehyde, m-maleimidobenzoyl-N-hydroxysuccinimide ester, carbodiumide and bis-biazotized benzidine. It is also understood that the peptide may be conjugated to a protein by genetic engineering techniques that are well known in the art.

As is also well known in the art, immunogenicity to a particular immunogen can be enhanced by the use of non-specific stimulators of the immune response known as adjuvants. Exemplary and preferred adjuvants include complete BCG, Detox, (RIBI, Immunochem Research Inc.) ISCOMS and aluminum hydroxide adjuvant (Superphos, Biosector).

Included in this invention are polyclonal antisera generated by using 28-kDa immunoreactive protein of *Ehrlichia canis* or a fragment of 28-kDa immunoreactive protein of *Ehrlichia canis* as the immunogen in, e.g., rabbits. Standard protocols for monoclonal and polyclonal antibody production known to those skilled in this art are employed. The monoclonal antibodies enerated by this procedure can be screened for the ability to identify recombinant *Ehrlichia canis* cDNA clones, and to distinguish them from known cDNA clones.

The invention encompasses not only an intact monoclonal antibody but also an immunologicailly-active antibody fragment, e.g., a Fab or $(Fab)_2$ fragment; an engineered single chain Fv molecule; or a chimeric molecule, e.g., an antibody which contains the binding specificity of one antibody, e.g., of murine origin, and the remaining portions of another antibody, e.g., of human origin.

In one embodiment, the antibody, or fragment thereof, may be linked to a toxin or to a detectable label, e.g. a radioactive label, non-radioactive isotopic label, fluorescent label. chemiluminescent label, paramagnetic label, enzyme label or calorimetric label. Those of ordinary skill in the art will know of these and other suitable labels which may be employed in accordance with the present invention. The binding of these labels to antibodies or fragments thereof can be accomplished using standard techniques commonly known to those of ordinary skill in the art.

It is also contemplated that pharmaceutical compositions may be prepared using the novel proteins of the present invention. In such a case, the pharmaceutical composition comprises the novel active composition(s) of the present invention and a pharmaceutically acceptable carrier. A person having ordinary skill in this art would readily be able to determine, without undue experimentation, the appropriate dosages and routes of administration of the active component of the present invention.

The phrase "pharmaceutically acceptable" refers to molecular entities and compositions that do not produce an allergic or similar untoward reaction when administered to a subject. The preparation of an aqueous composition that contains a protein as an active ingredient is well understood in the art. Typically, such compositions are prepared as injectables, either as liquid solutions or suspensions, solid forms suitable for solution in, or suspension in, liquid prior to injection can also be prepared. The preparation can also be emulsified.

A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidinie, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

In one embodiment of the present invention, there are provided DNA sequences encoding a 30-kDa immunoreactive protein of *Ehrlichia canis*. Preferably, the protein has an amino acid sequence selected from the group consisting of SEQ ID No. 2, 4, 6, 40, 42, 44, 46, and the gene has a nucleic acid sequence selected from the group consisting of SEQ ID No. 1, 3, 5, 39, 41, 43, 45 and is a member of a polymorphic multiple gene family. More preferably, the protein has an N-terminal signal sequence which is cleaved after post-translational process resulting in the production of a mature 28-kDa protein. Still preferably, the DNAs encoding 28-kDa proteins are contained in a single multigene locus, which has the size of 10,677 bp and encodes nine homologous 28-kDa proteins of *Ehrlichia canis*.

In another embodiment of the present invention, there is provided an expression vector comprising a gene encoding a 28-kDa immunoreactive protein of *Ehrlichia canis* and capable of expressing the gene when the vector is introduced into a cell.

In still another embodiment of the present invention, there is provided a recombinant protein comprising an amino acid sequence selected from the group consisting of SEQ ID No. 2, 4, 6, 40, 42, 44, 46. Preferably, the amino acid sequence is encoded by a nucleic acid sequence selected from the group consisting of SEQ ID No. 1, 3, 5, 39, 41, 43, 45. More preferably, the recombinant protein comprises four variable regions which are surface exposed, hydrophilic and antigenic. Still preferably, the recombinant protein is an antigen.

In yet another embodiment of the present invention, there is provided a method of producing the recombinant protein, comprising the steps of obtaining a vector that comprises an expression region comprising a sequence encoding the amino acid sequence selected from the group consisting of SEQ ID No. 2, 4, 6, 40, 42, 44, 46 operatively linked to a promoter; transfecting the vector into a cell; and culturing the cell under conditions effective for expression of the expression region.

The invention may also be described in certain embodiments as a method of inhibiting *Ehrlichia canis* infection in a subject comprising the steps of: identifying a subject suspected of being exposed to or infected with *Ehrlichia canis*; and administering a composition comprising a 28-kDa antigen of *Ehrlichia canis* in an amount effective to inhibit an *Ehrlichia canis* infection. The inhibition may occur through any means such as, i.e. the stimulation of the subject's humoral or cellular immune responses, or by other means such as inhibiting the normal function of the 28-kDa antigen, or even competing with the antigen for interaction with some agent in the subject's body.

The following examples are given for the purpose of illustrating various embodiments of the invention and are not meant to limit the present invention in any fashion.

EXAMPLE 1

Sequencing, Unknown 5' and 3' Regions of the ECa28-1 (p28-7) Gene

Ehrlichia and Purification *Ehrlichia canis* (Florida strain and isolates Demon, D J, Jake, and Fuzzy) were provided by Dr. Edward Breitschiwerdt, (College of Veterinary Medicine, North Carolina State University, Raleigh, N.C.). *E. canis* (Louisiana strain) was provided by Dr. Richard E. Corstvet (School of Veterinary Medicine, Louisiana State University, Baton Rouge, La.) and *E. canis* (Oklahoma strain) was provided by Dr. Jacqueline Dawson (Centers for Disease Control and Prevention, Atlanta. Ga.). Propagation of ehrlichiae was performed in DH82 cells with DMEM supplemented with 10% bovine calf serum and 2 mM L-glutamine at 37° C. The intracellular growth in DH82 cells was monitored by presence of *E. canis* morulae using general cytologic staining methods. Cells were harvested when 100% of the cells were infected with ehrlichiae and were then pelleted in a centrifuge at 17,000×g for 20 min. Cell pellets were disrupted with a Braun-Sonic 2000 sonicator twice at 40W for 30 sec on ice. Ehrlichiae were purified as described previously (Weiss et al., 1975). The lysate was loaded onto discontinuous gradients of 42%-36%-30% renografin, and centrifuged at 80,000×g for 1 hr. Heavy and light bands containing ehrlichiae were collected and washed with sucrose-phosphate-glutamate buffer (SPG, 218 mM sucrose, 3.8 mM $KH_2PO_4$, 7.2 m M $K_2HPO_4$, 4.9 mM glutamate, pH 7.0) and pelleted by centrifugation.

Nitucleic Acid Preparation *Ehrlichia canis* genomic DNA was prepared by resuspending the renografin-purified ehrlichiae in 600 µl of 10 mM Tris-HCl buffer (pH 7.5) with 1% sodium dodecyl sulfate (SDS, w/v) and 100 ng/ml of proteinasc K as described previously (McBride et al., 1996). This mixture was incubated for 1 hr at 56° C., and the nucleic acids were extracted twice with a mixture of phenol/chloroform/isoamyl alcohol (24:24:1). DNA was pelleted by absolute ethanol precipitation, washed once with 70% ethanol, dried and resuspended in 10 mM Tris (pH 7.5). Plasmid DNA was purified by using High Pure Plasmid Isolation Kit (Boehringer Mannheim, Indianapolis, Ind.), and PCR products were purified using a QIAquick PCR Purification Kit (Qiagen, Santa Clarita, Calif.).

Cloning of ECa28-1 (p28-7) Gene The full length sequence of p28-7 gene was determined using a Universal GenomeWalker Kit (CLONTECH, Palo Alto, Calif.) according to the protocol supplied by the manufacturer. Genomic *E. canis* (Jake isolate) DNA was digested completely with five restriction enzymes (DraI, EcoRV, PvuII, ScaI, StuI) which produce blunt-ended DNA. An adapter (AP1) supplied in the kit was ligated to each end of *E. canis* DNA. The genornic libraries were used as templates to find the unknown DNA sequence of the p28-7 gene by PCR using a primer complementary to a known portion of the p28-7 sequence and a primer specific for the adapter AP1. Primers specific for p28-7 used for genome walking were designed from the known DNA sequence derived from PCR amplification of p28-7 with primers 793 (SEQ ID NO. 16) and 1330 (SEQ ID NO. 17). Primers 394 (5'-GCATTTCCACAGGATCATAGGTAA-3'; nucleotides 687–710, SEQ ID NO. 21) and 394C (5'-TTACCTATGATCCTGT GGAAATGC-3; nucleotides 710–687, SEQ ID NO. 22) were used in conjunction with supplied primer AP1 to amplify the unknown 5' and 3' regions of the p28-7 gene by PCR. A PCR product corresponding to the 5' region of the p28-7 gene amplified with primers 394C and AP1 (2000-bp) was sequenced unidirectionally with primer 793C (5'-GAGTA ACCAACAGCTCCTGC-3', SEQ ID No. 23). A PCR product corresponding to the 3' region of the p28-7 gene amplified with primers 394 and AP1 (580-bp) was sequenced bidirectionally with the same primers. Noncoding regions on the 5' and 3' regions adjacent to the open reading frame were sequenced, and primers EC28OM-F (5'-TCTACTTTGCACTTCC ACTATTGT-3', SEQ ID NO. 24) and EC28OM-R (5'-ATTCTTTTGCCACTATTT TTCTTT-3', SEQ ID NO. 25) complementary to these regions were designed in order to amplify the entire p28-7 gene.

DNA Sequencing DNA was sequenced with an ABI Prism 377 DNA Sequencer (Perkin-Elmer Applied Biosystems, Foster City. Calif.). The entire p28-7 genes of seven *E. canis* isolates (tour from North Carolina, and one each from Oklahoma, Florida and Louisiana) were amplified by PCR with primers EC28OM-F (SEQ ID No. 24) and EC28OM-R (SEQ ID No. 25) with a thermal cycling profile of 95° C. for 5 minutes, and 30 cycles of 95° C. for 30 seconds, 62° C. for 1 minutes, and 72° C. for 2 minutes and a 72° C. extension for 10 minutes. The resulting PCR products were bidirectionally sequenced with the same primers.

EXAMPLE 2

PCR Amplification, Cloning, Sequencing and Expression of *E. canis* ECa28-1 (p28-7) Gene Expressing Vectors The entire *E. canis* p28-7 gene was PCR-amplified with primers-EC28OM-F and EC28OM-R and cloned into pCR2.1-TOPO TA cloning vector to obtain the desired set of restriction enzyme cleavage sites (Invitrogen, Carlsbad, Calif.). The insert was excised from pCR2.1-TOPO with BstX 1 and ligated into pcDNA 3.1 eukaryotic expression vector (Invitrogen, Carlsbad, Calif.) designated pcDNA3.1/EC28 for subsequent studies. The pcDNA3.1/EC28 plasmid was amplified, and the gene was excised with a KpnI-XbaI double digestion and directionally ligated into pThioHis prokaryotic expression vector (Invitrogen, Carlsbad, Calif.). The clone (designated pThioHis/EC28) produced a recombinant thioredoxin fusion protein in Escherichia coli BL21. The recombinant fusion protein was crudely purified in the insoluble phase by centrifugation. The control thioredoxin fusion protein was purified from soluble cell lysates under native conditions using nickel-NTA spin columns (Qiagen, Santa Clarita, Calif.).

Western Blot Analysis Recombinant E. canis p28-7 fusion protein was subjected to SDS-polyacrylamide gel electrophoresis (SDS-PAGE) on 4–15% Tris-HCl gradient gels (Bio-Rad, Hercules, Calif.) and transferred to pure nitrocellulose (Schleicher & Schuell, Keene, N. H.) using a semi-dry transfer cell (Bio-Rad, Hercules, Calif.). The membrane was incubated with convalescent phase antisera from an E. canis-infected dog diluted 1:5000 for 1 hour, washed, and then incubated with an anti-canine IgG (H & L) alkailine phosphatase-conjuglited affinity-purified secondary antibody at 1:1000 for 1 hour (Kirkegaard & Perry Laboratories, Gaithersburg, Md.). Bound antibody was visualized with 5-bromo-4-chloro-3-indolyl phosphate/nitiroblue tetrazolum (BCIP/NBT) substrate (Kirkegaard & Perry Laboratories, Gaithersburg, Md.).

Southern Blot Analysis to determine if multiple genes homologous to the p28-7 gene were present in the E. canis genome, a genomic Southern blot analysis was performed using a standard procedure (Sambrook et al. 1989). E. canis genomic DNA digested completely with each of the restriction enzymes BanII, EcoRV, HaeII, KpnI and SpeI, which do not cut within the p28-7 gene, and AseI which digests p28-7 at nucleotides 34, 43 and 656. The probe was produced by PCR amplification with primers EC28OM-F and EC28OM-R and digoxigenin (DIG)-labeled deoxynucleotide triphosphates (dNTPs) (Boehringer Mannheim, Indianapolis, Ind.) and digested with AseI. The digested probe (566-bp) was separated by agarose gel electrophoresis, gel-purified and then used for hybridization. The completely digested genomic E canis DNA was electrophoresed and transferred to a nylon membrane (Boehringer Mannheim, Indianapolis, Ind.) and hybridized at 40° C. for 16 hr with the p28-7 gene DIG-labeled probe in DIG Easy Hyb buffer according to the manufacturer's protocol (Boehringer Mannheim, Indianapolis. Ind.). Bound probe was detected with a anti-DIG alkaline phosphatase-conjugated antibody and a luminescent substrate (Boehringer Mannheim, Indianapolis, Ind.) and exposed to BioMax scientific imaging film (Eastman Kodak, Rochester, N.Y.).

Sequence Analysis and Comparasion E. chaffeensis p28 and C. ruminantium map-1 DNA sequences were obtained from the National Center of Biotechnology Information (NCBI). Nucleotide and deduced amino acid sequences, and protein and phylogenetic analyses were performed with LASERGENE software (DNASTAR, Inc., Madison, Wis.). Analysis of post-translational processing was performed by the method of McGeoch and von Heijne for signal sequence recognition using the PSORT program (McGeoch, 1985; von Heijne, 1986)

Sequence analysis of p28-7 from seven different strains of E. canis was performed with primers designed to amplify the entire gene. Analysis revealed the sequence of this gene was conserved among the isolates from North Carolina (four), Louisiana. Florida and Oklahoma.

Results

Alignment of nucleic acid sequences from E. chaffeensis p28 and Cowdria ruminantium map-1 using the Jotun-Hein aligorithm produced a consensus sequence with regions of high homology (>90%). These homologous regions (nucleotides 313–332 and 823–843 of C. ruminantium map-1; 307–326 and 814–834 of E. chaffeensis p28) were targeted as primer annealing sites for PCR amplification. PCR amplification of the E. canis p28-7 gene was accomplished with primers 793 (5-GCAGGAGCTGTTGGTTACTC-3') (SEQ ID NO. 16) and 1330 (5'-CCTTCCTCCAAGTTCTATGCC-3') (SEQ ID NO. 17), resulting in a 518-bp PCR product. E. canis DNA was amplified with primers 793 and 1330 with a thermal cycling profile of 95° C. for 2 min, and 30 cycles of 95° C. for 30 sec, 62° C. for 1 min, 72° C. for 2 min followed by a 72° C. extension for 10 min and 4° C. hold. The nucleic acid sequence of the E. canis PCR product was obtained by sequencing the product directly with primers 793 and 1330.

Analysis of the sequence revealed an open reading frame encoding a protein of 170 amino acids, and alignment of the 518-bp sequence obtained from PCR amplification of E. canis with the DNA sequence of E. chaffeensis p28 gene revealed a similarity greater than 70%, indicating that the genes were homologous.

Adapter PCR with primers 394 and 793C was performed to determine the 5' and 3' segments of the sequence of the entire gene. Primer 394 produced four PCR products (3-kb, 2-kb, 1-kb, and 0.8-kb), and the 0.8-bp product was sequenced bidirectionally using primers 394 and API. The deduced sequence overlapped with the 3' end of the 518-bp product, extending the open reading frame 12-bp to a termination codon. An additional 625-bp of non-coding sequence at the 3' end of the p28-7 gene was also sequenced.

Primer 394C was used to amplify the 5' end of the p28-7 gene with supplied primer AP1. Amplification with these primers resulted in three PCR products (3.3, 3-kb, and 2-kb). The 2-kb fragment was sequenced unidirectionally with primer 793C. The sequence provided the putative start codon of the p28-7 gene and completed the 834-bp open reading frame encoding a protein of 278 amino acids. An additional 144-bp of readable sequence in the 5' noncoding region of the p28-7 gene was generated. Primers EC28OM-F and EC28OM-R were designed from complementary non-coding regions adjacent to the p28-7 gene.

Figure 2:
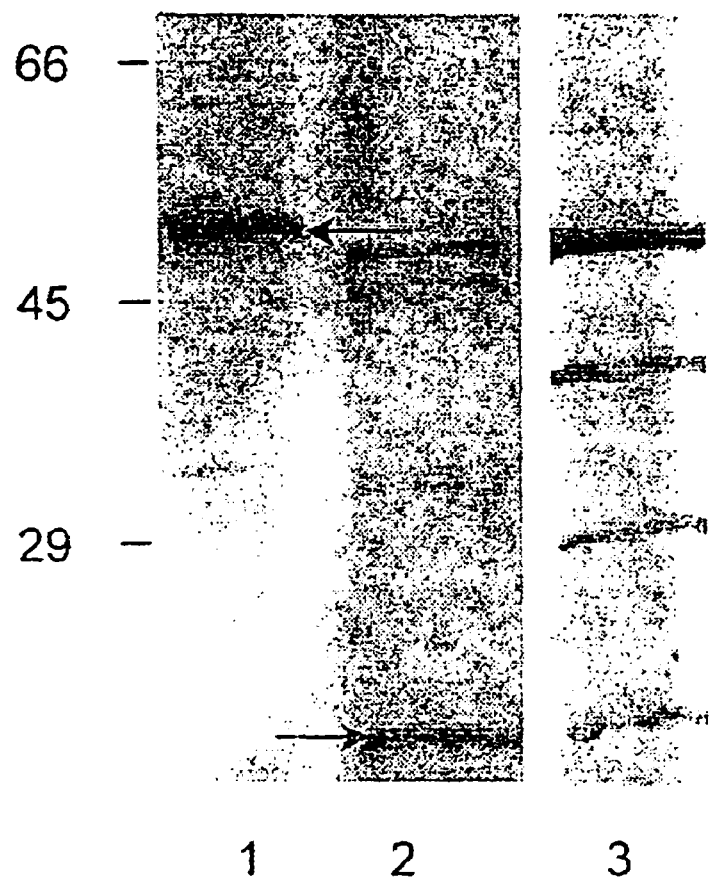
FIG. 2 shows SDS-PAGE of expressed 50-kDa recombinant p28-7-thioredoxin fusion protein (Lane 1, arrow) and 16-kDa thioredoxin control (Lane 2, arrow), and corresponding immunoblot of recombinant p28-7-thioredoxin fusion protein recognized by covalescent-phase E. canis canine antiserum (Lane 3). Thioredoxin control was not detected by E. canis antiserum (not shown).

The PCR product amplified with these primers was sequenced directly with the same primers. The complete DNA sequence for the E. canis p28-7 gene (SEQ ID NO. 1) is shown in FIG. 1. The p28-7 PCR fragment amplified with these primers contained the entire open reading frame and 17 additional amino acids from the 5' non-coding primer region. The gene was directionally subcloned into pThioHis expression vector, and E. coli (BL21) were transformed with this construct. The expressed p28-7-thioredoxin fusion protein was insoluble. The expressed protein had an additional 114 amino acids associated with the thioredoxin, 5 amino acids for the enterokinase recognition site, and 32 amino acids from the multiple cloning site and 5' non-coding primer region at the N-terminus. Convalescent-phase antiserum from an E. canis infected dog recognized the expressed recombinant fusion protein, but did not react with the thioredoxin control (FIG. 2).

EXAMPLE 3

Sequence Homology of E. canis p28-7 Gene

The nucleic acid sequence of E. canis p28-7 (834-bp) and the E. chaffeensis omp-1 family of genes including signal sequences (p28-7, omp-1A, B, C, D, E, and F) were aligned using the Clustal method to examine homology between these genes (alignment not shown). Nucleic acid homology was equally conserved (68.9%) between E. canis p28-7, E. chaffeensis p28 and omp-1F. Other putative outer membrane protein genes in the E. chaffeensis omp-1 family, omp-1D (68.2%), omp-1E (66.7%), omp-1C (64.1%), Cowdria ruminantium map-1 (61.8%), E. canis 28-kDa protein 1 gene (60%) and 28-kDa protein 2 gene (partial) (59.5%) were also homologous to p28-7. E. chaffeensis omp-1B had the least nucleic acid homology (45.1%) with E. canis p28-7.

Figure 3B:
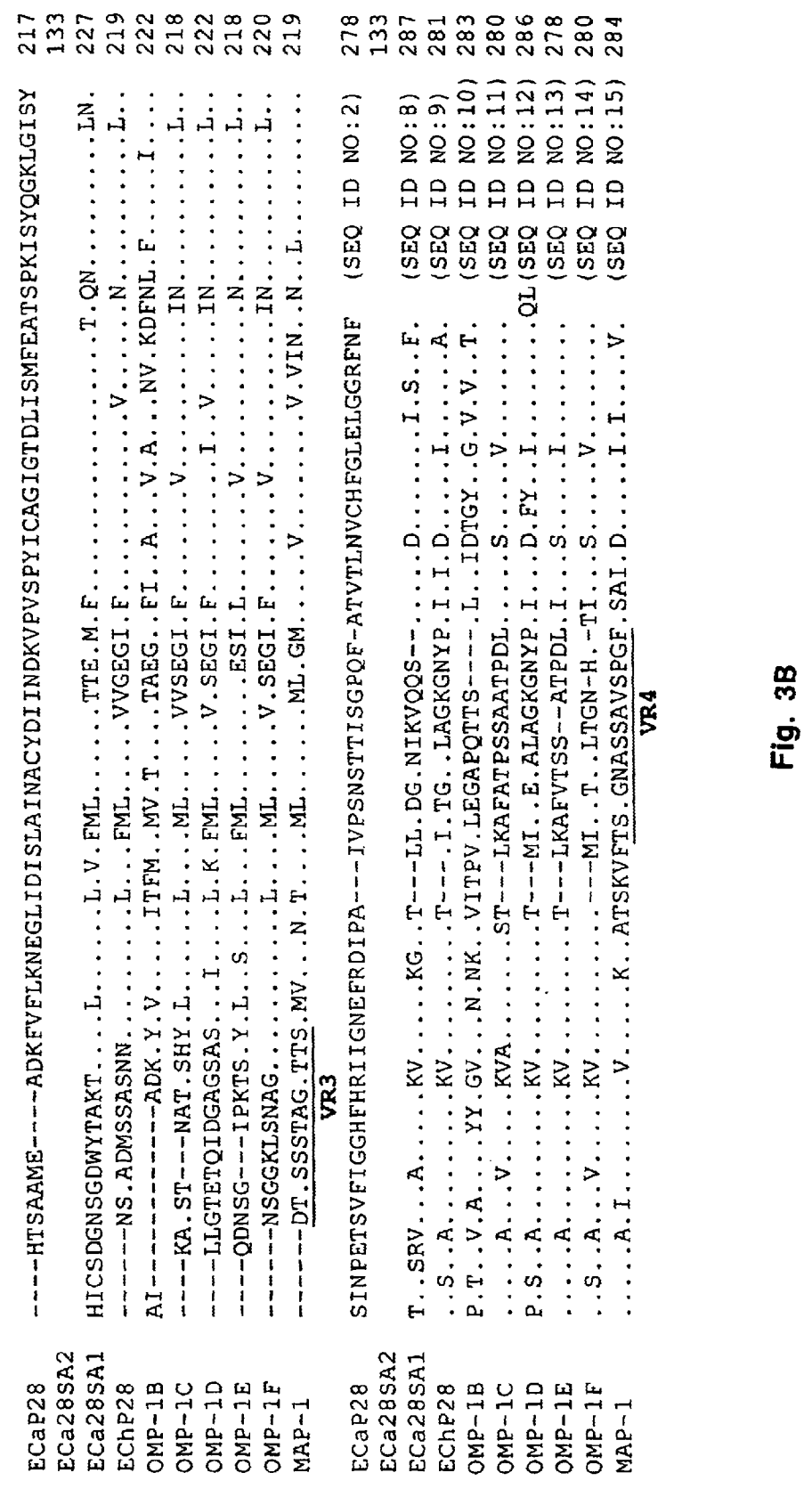
Figure 4:
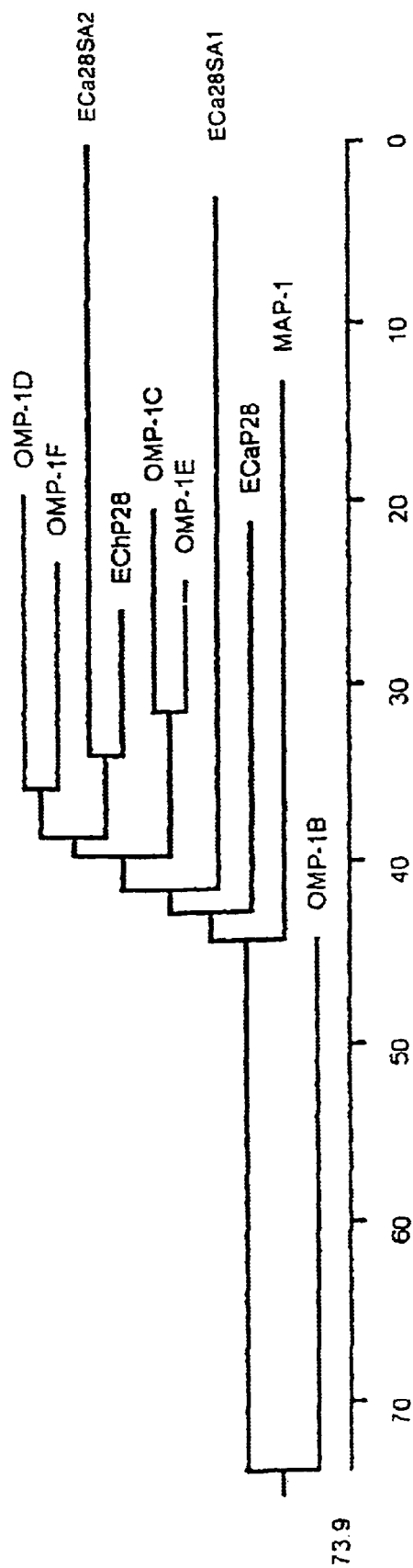
FIG. 4 shows phylogenetic relatedness of E. canis p28-7 (ECa28-1), p28-5 (ECa28SA2, partial sequence), p28-4 (ECa28SA1), members of the E. chaffeensis omp-1 multiple gene family, and C. rumanintium map-1 protein from deduced amino acid sequences utilizing unbalanced tree construction. The length of each pair of branches represents the distance between the amino acid sequence of the pairs. The scale measures the distance between sequences.

Alignment of the predicted amino acid sequences of E. canis P28-7 (SEQ ID NO. 2) and E. chaffeensis P28 revealed amino acid substitutions resulting in four variable regions (VR). Substitutions or deletions in the amino acid sequence and the locations of variable regions of E. canis P28-7 and the E. chaffeensis OMP-1 family were identified (FIG. 3). Amino acid comparison including the signal peptide revealed that E. canis P28-7 shared the most homology with OMP-1F (68%) of the E. chaffeensis OMP-1 family, followed by E. chaffeensis P28 (65.5%), OMP-1E (65.1%). OMP-1D (62.9%), OMP-1C (62.9%), Cowdria ruminantium MAP-1 (59.4%), E. canis 28-kDa protein 1 (55.6%) and 28-kDa protein 2 (partial) (53.6%), and OMP-1B (43.2%). The phylogenetic relationships based on amino acid sequences show that E. canis P28-7 and C. ruminantium MAP-1, E. chaffeensis OMP-1 proteins, and E. canis 28-kDa proteins 1 and 2 (partial) are related (FIG. 4).

EXAMPLE 4

Predicted Surface Probability and Immunoreactivity of E. canis P28-7

Figure 6:
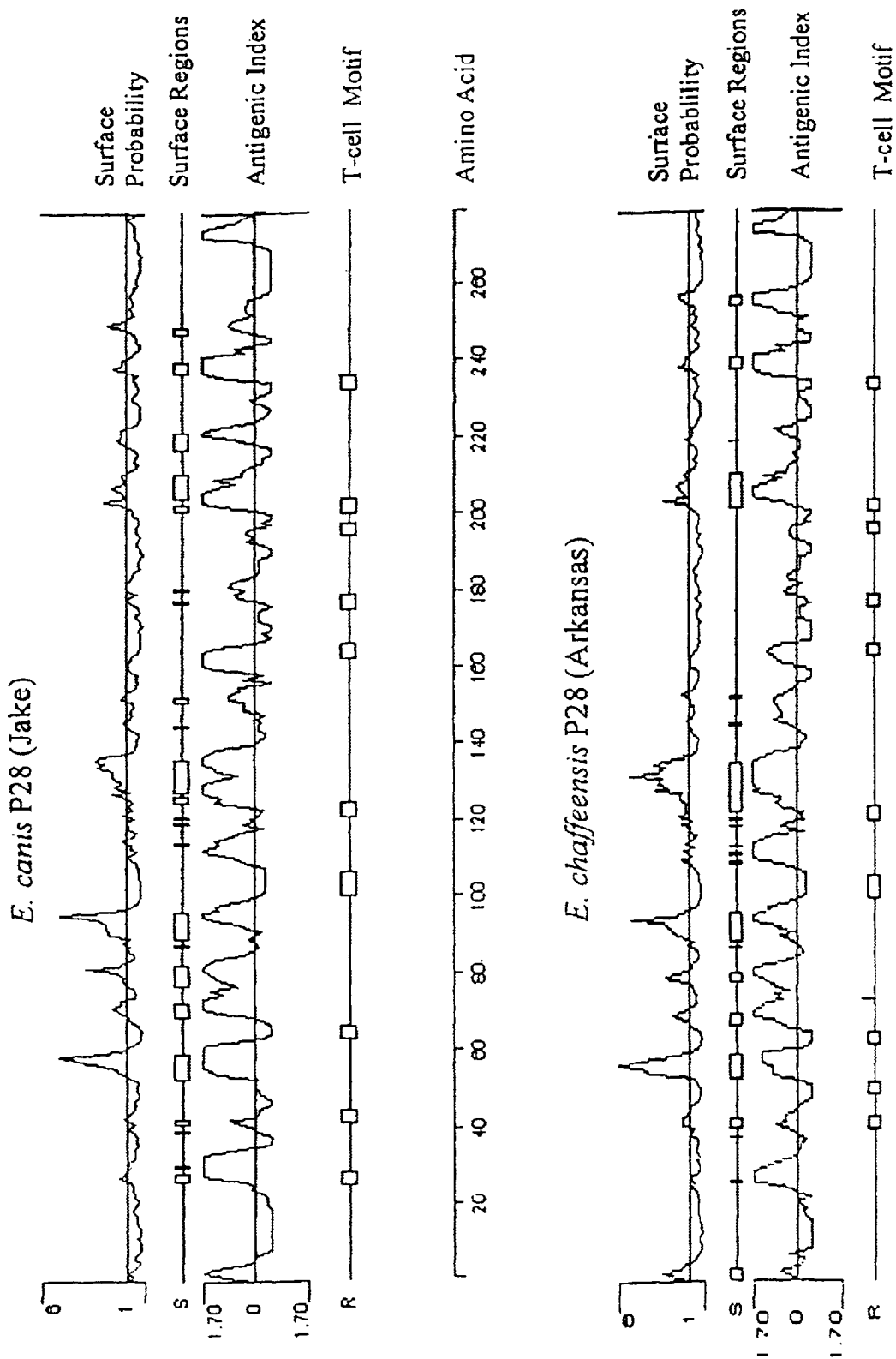
FIG. 6 shows comparison of predicted protein characteristics of E. canis p28-7 (ECa28-1, Jake strain) and E. chaffeensis P28 (Arkansas strain). Surface probability predicts the surface residues by using a window of hexapeptide. A surface residue is any residue with a >2.0 nm$^2$ of water accessible surface area. A hexapeptide with a value higher than 1 was considered as surface region. The antigenic index predicts potential antigenic determinants. The regions with a value above zero are potential antigenic determinants. T-cell motif locates the potential T-cell antigenic determinants by using a motif of 5 amino acids with residue 1-glycine or polar, residue 2-hydrophobic, residue 3-hydrophobic, residue 4-hydrophobic or proline, and residue 5-polar or glycine. The scale indicates amino acid positions.

Analysis of E. canis P28-7 using hydropathy and hydrophilicity profiles predicted surface-exposed regions on P28-7 (FIG. 6). Eight major surface-exposed regions consisting of 3 to 9 amino acids were identified on E. canis P28-7 and were similar to the profile of surface-exposed regions on E. chaffeensis P28 (FIG. 6). Five of the larger surface-exposed regions on E. canis P28-7 were located in the N-terminal region of the protein. Surface-exposed hydrophilic regions were found in all four of the variable regions of E. canis P28-7. Ten T-cell motifs were predicted in the P28-7 using the Rothbard-Taylor aligorithm (Rothbard and Taylor, 1988), and high antigenicity of the E. canis P28-7 was predicted by the Jameson-Wolf antigenicity aligorithm (FIG. 6) (Jameson and Wolf, 1988). Similarities in antigenicity and T-cell motifs were observed between E. canis P28-7 and E. chaffeensis P28.

EXAMPLE 5

Detection of Homologous Genomic Copies of E. canis p28-7 Gene

Figure 5:
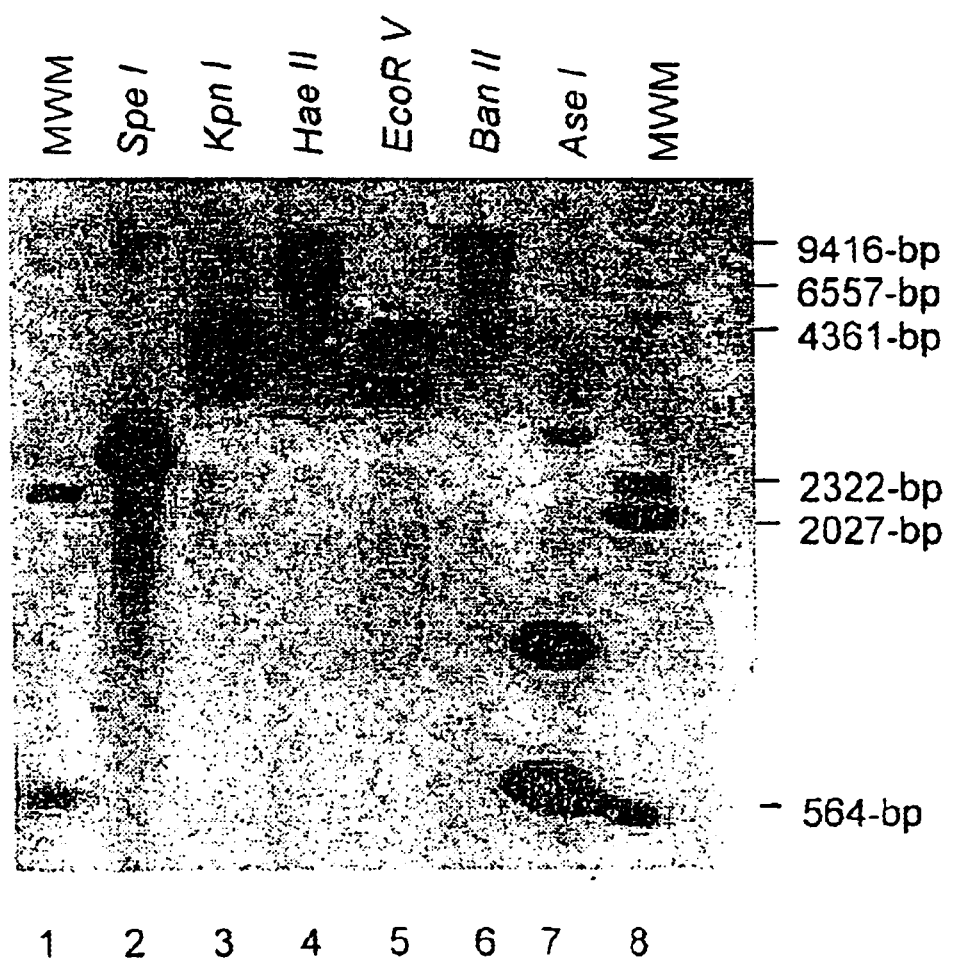
FIG. 5 shows Southern blot analysis of E. canis genomic DNA completely digested with six individual restriction enzymes and hybridized with a p28-7 DIG-labeled probe (Lanes 2–7); DIG-labeled molecular weight markers (Lanes 1 and 8).

Genomic Southern blot analysis of E. canis DNA completely digested independently with restriction enzymes BanII, EcoRV, HaeII, KpnI, SpeI, which do not have restriction endonuclease sites in the p28-7 gene, and AseI, which has internal restriction endonuclease sites at nucleotides 34, 43 and 656, revealed the presence of at least three homologous p28-7 gene copies (FIG. 5). Although E. canis p28-7 has internal Ase I internal restriction sites, the DIG-labeled probe used in the hybridization experiment targeted a region of the gene within a single DNA fragment generated by the AseI digestion of the gene. Digestion with AseI produced 3 bands (approximately 566-bp, 850-bp, and 3-kb) that hybridized with the p28-7 DNA probe indicating the presence of multiple genes homologous to p28-7 in the genome. Digestion with EcoRV and SpeI produced two bands that hybridized with the p28-7 gene probe.

EXAMPLE 6

PCR Amplification of E. canis ECa28SA2 (p28-5), ECa28SA3 (p28-6) Genes and Identification of the Multiple Gene Locus In order to specifically amplify possible unknown genes downstream of ECa28SA2 (p28-5), primer 46f specific for p28-5 (5'-ATATACTTCCTACCTAATGTCTCA-3', SEQ ID No. 18), and primer 1330 (SEQ ID No. 17) which targets a conserved region on the 3' end of p28-7 gene were used for amplification. The amplified product was gel purified and cloned into a TA cloning vector (Invitrogen, Santa Clarita, Calif.). The clone was sequenced bidirectionally with primers: M13 reverse from the vector, 46f, ECa28SA2 (5'-AGTGCAGAGTCTTCGGTTTC-3', SEQ ID No. 19), ECa5.3 (5'-GTTACTTGCGGAGGACAT-3', SEQ ID No. 20). DNA was amplified with a thermal cycling profile of 95° C. for 2 min, and 30 cycles of 95° C. for 30 sec, 48° C. for 1 min, 72° C. for 1 min followed by a 72° C. extension for 10 min and 4° C. hold.

A 2-kb PCR product was amplified with these primers that contained 2 open reading frames. The first open reading frame contained the known region of the p28-5 gene and a previously unsequenced 3' portion of the gene. Downstream from p28-5 an additional non identical, but homologous 28-kDa protein gene was found, and designated ECa28SA3 (p28-6).

Specific primers designated ECaSA3-2 (5'-CTAGGATTA GGTTATAGTATAAGTT-3', SEQ ID No. 26) corresponding to regions within p28-6 and primer 793C (SEQ ID No. 23) which anneals to a region with p28-7 were used to amplify the intergenic region between gene p28-6 and p28-7. DNA was amplified with a thermal cycling profile of 95° C. for 2 min, and 30 cycles of 95° C. for 30 sec, 50° C. for 1 min, 72° C. for 1 min followed by a 72° C. extension for 10 min and 4° C. hold.

Figure 8:
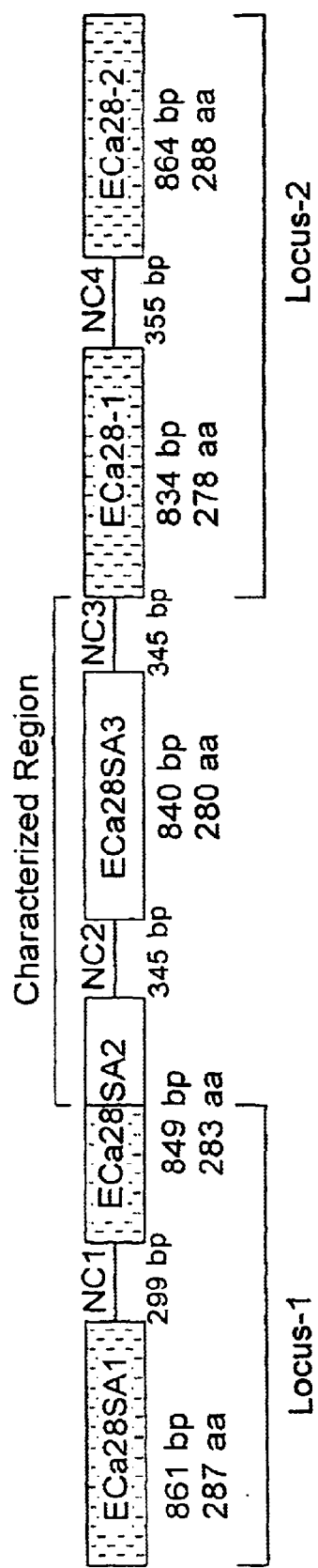
FIG. 8 shows schematic of the E. canis 28-kDa protein gene locus (5.592-Kb, containing five genes) indicating genomic orientation and intergenic noncoding regions (28NC1-4). The 28-kDa protein genes shown in Locus 1 and 2 (shaded) have been described (McBride et al., 1999; Reddy et al., 1998; Ohashi et al., 1998). The complete sequence of p28-5 and a new 28-kDa protein gene designated p28-6 was sequenced. The noncoding intergenic regions (28NC2-3) between p28-5, p28-6 and p28-7 were completed joining the previously unlinked loci 1 and 2.

An 800-bp PCR product was amplified which contained the 3' end of p28-6, the intergenic region between p28-6 and p28-7 (28NC3) and the 5' end of p28-7, joining the previously separate loci (FIG. 8). The 849-bp open reading frame of p28-5 encodes a 283 amino acid protein, and p28-6 has an 840-bp open reading frame encoding a 280 amino acid protein. The intergenic noncoding region between p28-6 and p28-7 was 345-bp in length (FIGS. 7 and 8)

EXAMPLE 7

Figure 9:
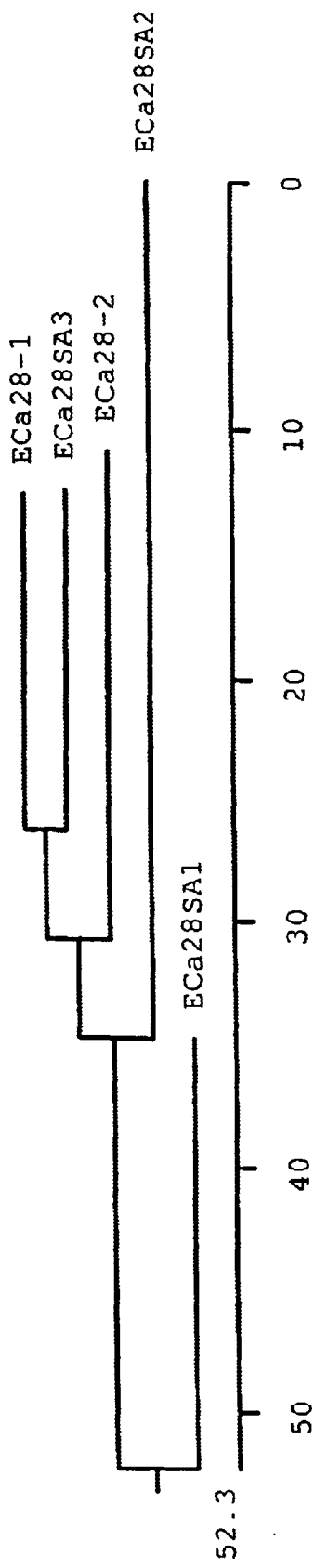
FIG. 9 shows phylogenetic relatedness of the E. canis 28-kDa protein gene p28-4 (ECa28SA1), p28-5 (ECa28SA2), p28-6 (ECa28SA3), p28-7 (ECa28-1) and p28-8 (ECa28-2) based on amino acid sequences utilizing, unbalanced tree construction. The length of each pair of branches represents the distance between amino acid pairs. The scale measures the distance between sequences.

Nucleic and Amino Acid Homology of E. canis p28-4, p28-5, p28-6, p28-7 and p28-8 proteins The nucleic and amino acid sequences of all five E. canis 28-kDa protein genes were aligned using the Clustal method to examine the homology between these genes. The nucleic acid homology ranged from 58 to 75% and a similar amino acid homology of ranging from 67 to 72% was observed between the *E. canis* 28-kDa protein gene members (FIG. 9).

Transcriptional Promoter Regions The intergenic regions between the 28-kDa protein genes were analyzed for promoter sequences by comparison with consensus *Escherichia coli* promoter regions and a promoter from *E. chaffeensis* (Yu et al., 1997; McClure, 1985). Putative promoter sequences including RBS, −10 and −35 regions were identified in 4 intergenic sequences corresponding to genes p28-5, p28-6, p28-7, and p28-8 (ECa28-2) (FIG. 10). The upstream noncoding region of p28-4 (ECa28SA1) is not known and was not analyzed.

N-Terminal Signal Sequence the amino acid sequence analysis revealed that entire *E. canis* p28-7 has a deduced molecular mass of 30.5-kDa and the entire p28-6 has a deduced molecular mass of 30.7-kDa. Both proteins have a predicted N-terminal signal peptide of 23 amino acids (MNCKKILITTALMSLMYYAPSIS, SEQ ID No. 27), which is similar to that predicted for *E. chaffeensis* P28 (MNYKKITSALISLISSLPGV SFS, SEQ ID NO. 28), and the OMP-1 protein family (Yu et al., 1999a; Ohashi et al., 1998b).

A preferred cleavage site for signal peptidases (SIS; Ser-X-Ser) (Oliver, 1985) is found at amino acids 21, 22, and 23 of p28-7. An additional putative cleavage site at amino acid position 25 (MNCKKILITTALISLMYSIPSISSFS, SEQ ID NO. 29) identical to the predicted cleavage site of *E. chaffeensis* P28 (SFS) was also present, and would result in a mature p28-7 with a predicted molecular mass of 27.7-kDa. Signal cleavage site of the previously reported partial sequence of p28-5 is predicted at amino acid 30. However, signal sequence analysis predicted that p28-4 had an uncleavable signal sequence.

SUMMARY

Proteins of similar molecular mass have been identified and cloned from multiple rickettsial agents including *E. canis, E. chaffeensis,* and *C. ruminantium* (Reddy et al., 1998; Jongejan et al., 1993; Ohashi et al., 1998). A single locus in *Ehrlichia chaffeensis* with 6 homologous p28 genes, and 2 loci in *E. canis*, each containing some homologous 28-kDa protein genes have been previously described.

The present invention demonstrated the cloning, expression and characterization of genes encoding mature 28-kDa proteins of *E. canis* that are homologous to the omp-1 multiple gene family of *E. chaffeensis* and the *C. ruminantium* map-1 gene. Two new 28-kDa protein genes were identified, p28-7 and p28-6. Another *E. canis* 28-kDa protein gene, p28-5, partially sequenced previously (Reddy et al., 1998), was sequenced completely in the present invention. Also disclosed is the identification and characterization of a single locus in *E. canis* containing five *E. canis* 28-kDa protein genes (p28-4, p28-5, p28-6, p28-7 and p28-8).

The *E. canis* 28-kDa proteins are homologous to *E. chaffeensis* OMP-1 family and the MAP-1 protein of *C. rumanintium*. The most homologous *E. canis* 28-kDa proteins (p28-6, p28-7 and p28-8) are sequentially arranged in the locus. Homology of these proteins ranged from 67.5% to 72.3%. Divergence among these 28-kDa proteins was 27.3% to 38.6%. *E. canis* 28-kDa proteins p28-4 and p28-5 were the least homologous with homology ranging from 50.9% to 59.4% and divergence of 53.3 to 69.9%. Differences between the genes lies primarily in the four hypervariable regions and suggests that these regions are surface exposed and subject to selective pressure by the immune system.

Conservation of p28-7 among seven *E. canis* isolates has been reported (McBride et al., 1999), suggesting that *E. canis* may be clonal in North America. Conversely, significant diversity of p28 among *E. chaffeensis* isolates has been reported (Yu et al., 1999a).

All of the *E. canis* 28-kDa proteins appear to be post translationally processed from a 30-kD protein to a mature 28-kD protein. Recently, a signal sequence was identified on *E. chaffeensis* P28 (Yu et al., 1999a), and N-terminal amino acid sequencing has verified that the protein is post-translationally processed resulting in cleavage of the signal sequence to produce a mature protein (Ohashi et al., 1998). The leader sequences of OMP-1F and OMP-1E have also been proposed as leader signal peptides (Ohashi et al., 1998). Signal sequences identified on *E. chaffeensis* OMP-1F, OMP-1E and P28 are homologous to the leader sequence of *E. canis* 28-kDa protein. Promoter sequences for the p28 genes have not been determined experimentally, but putative promoter regions were identified by comparison with consensus sequences of the RBS, −10 and −35 promoter regions of *E. coli* and other ehrlichiae (Yu et al., 1997; McClure, 1985). Such promoter sequences would allow each gene to potentially be transcribed and translated, suggesting that these genes may be differentially expressed in the host. Persistence of infection in dogs may be related to differential expression of p28 genes resulting in antigenic changes in vivo, thus allowing the organism to evade the immune response.

The *E. canis* 28-kDa protein genes were found to exhibit nucleic acid and amino acid sequence homology with the *E. chaffeensis* omp-1 gene family and *C. ruminantium* map-1 gene. Previous studies have identified a 30-kDa protein of *E. canis* that reacts with convalescent phase antisera against *E. chaffeensis*, but was believed to be antigenically distinct (Rikihisa et al. 1994). Findings based on comparison of amino acid substitutions in four variable regions of *E. canis* 28-kDa proteins support this possibility. Together these findings also suggest that the amino acids responsible for the antigenic differences between *E. canis* and *E. chaffeensis* P28 are located in these variable regions and are readily accessible to the immune system.

It was reported that immunoreactive peptides were located in the variable regions of the 28-kDa proteins of *C. rumanintium, E. chaffeensis* and *E. canis* (Reddy et al., 1998). Analysis of *E. canis* and *E. chaffeensis* P28 revealed that all of the variable regions have predicted surface-exposed amino acids. A study in dogs demonstrated lack of cross protection between *E. canis* and *E. chaffeensis* (Dawson and Ewing, 1992). This observation may be related to antigenic differences in the variable regions of P28 as well as in other immunologically important antigens of these ehrlichial species. Another study found that convalescent phase human antisera from *E. chaffeensis*-infected patients recognized 29/28-kDa protein(s) of *E. chaffeensis* and also reacted with homologous proteins of *E. canis* (Chen et al., 1997). Homologous and crossreactive epitopes on the *E. canis* 28-kDa protein and *E. chaffeensis* P28 appear to be recognized by the immune system.

*E. canis* 28-kDa proteins may be important immunoprotective antigens. Several reports have demonstrated that the 30-kDa antigen of *E. canis* exhibits strong immunoreactivity (Rikihisa et al., 1994; Rikihisa et al., 1992). Antibodies in convalescent phase antisera from humans and dogs have consistently reacted with proteins in this size range from *E. chaffeensis* and *E. canis*, suggesting that they may be important immunoprotective antigens (Rikihisa et al., 1994; Chen et al., 1994; Chen et al., 1997). In addition, antibodies to 30, 24 and 21-kDa proteins developed early in the immune response to *E. canis* (Rikihisa et al., 1994; Rikihisa et al., 1992), suggesting that these proteins may be especially important in the immune responses in the acute stage of disease. Recently, a family of homologous genes encoding outer membrane proteins with molecular masses of 28-kDa have been identified in *E. chaffeensis*, and mice immunized with recombinant *E. chaffeensis* P28 appeared to have developed immunity against homologous challenge (Ohashi et al., 1998). The P28 of *E. chaffeensis* has been demonstrated to be present in the outer membrane, and immunoelectron microscopy has localized the P28 on the surface on the organism, and thus suggesting that it may serve as an adhesin (Ohashi et al., 1998). It is likely that the 28-kDa proteins of *E. canis* identified in this study have the same location and possibly serve a similar function.

Comparison of p28-7 from different strains of *E. canis* revealed that the gene is apparently completely conserved. Studies involving *E. chaffeensis* have demonstrated immunologic and molecular evidence of diversity. Patients infected with *E. chaffeensis* have variable immunoreactivity to the 29/28-kDa proteins, suggesting that there is antigenic diversity (Chen et al., 1997). Recently molecular evidence has been generated to support antigenic diversity in the p28 gene from *E. chaffeensis* (Yu et al., 1999a). A comparison of five *E. chaffeensis* isolates revealed that two isolates (Sapulpa and St. Vincent) were 100% identical, but three others (Arkansas, Jax, 91HE17) were divergent by as much as 13.4% at the amino acid level. The conservation of *E. canis* p28-7 suggests that *E. canis* strains found in the United States may be genetically identical and thus *E. canis* 28-kDa protein is an attractive vaccine candidate for canine ehrlichiosis in the United States. Further analysis of *E. canis* isolates outside the United States may provide information regarding the origin and evolution of *E. canis*. Conservation of the 28-kDa protein makes it an important potential candidate for reliable serodiagnosis of canine ehrlichiosis.

The role of multiple homologous genes is not known at this point; however, persistence of *E. canis* infections in dogs could conceivably be related to antigenic variation due to variable expression of homologous 28-kDa protein genes, thus enabling *E. canis* to evade immune surveillance. Variation of msp-3 genes in *A. marginale* is partially responsible for variation in the MSP-3 protein, resulting in persistent infections (Alleman et al., 1997). Studies to examine 28-kDa protein gene expression by *E. canis* in acutely and chronically infected dogs would provide insight into the role of the 28-kDa protein gene family in persistence of infection.

EXAMPLE 8

Identification of *E. canis* p28-1, p28-2, p28-3 and p28-9 Genes

Unknown regions of DNA upstream and downstream of the five gene locus of tandemly arranged p28 genes described above were sequenced by designing gene specific primers for p28-1 (ECa28-75C) and p28-5 (ECa28-5-818f) to extend the p28 gene locus bidirectionally. Multiple gene walks were performed to obtain the unknown sequence as follows: 1.9-kp downstream of the 5 gene locus was amplified and sequenced using primers p28-5-818f (5'-TTA AAC ATA TGC CAC TTC GGA CTA-3', SEQ ID No. 34), producing a 900-bp amplicon, and 1191 (5'-TAT GAT CGT GTA AAA TTG CTG TGA GTA T-3', SEQ ID No. 35), producing a 1-kb amplicon. The 3.67-kbp of DNA upstream of the five gene locus was amplified and sequenced with primers ECa28-75C (5'-TAC TGG CAC GTG CTG GAC TA-3', SEQ ID No. 36), producing a 1.6-kbp amplicon; ECa5'-1600 (5'-CAC CAA TAA ATG CAG AGA CTT C-3', SEQ ID No. 37), producing a 1.6-kbp amplicon; and 3125 (5'-AAT CCA TCA TTT CTC ATT ACA GTG-TG-3', SEQ ID No. 38), producing a 800-bp amplicon. The locus of nine tandemly arranged genes consisting of the four new p28 genes, and the five p28 genes described above were designated p28-1 through p28-9 (FIG. 11).

The nucleic acid and amino acid sequences of the *E. canis* p28 genes were aligned using the Clustal method to examine the homology between these genes. Homology of these proteins ranged from 67.5% to 75%, and divergence among these P28 proteins was 26.9% to 38%. *E. canis* P28 proteins P28-1, P28-2, and P28-9 were the least homologous with the other p28 genes ranging from 37% to 49% and divergence of 53 to 77%. The nucleic acid homology of the nine p28 genes ranged from 28 to 72%. The phylogenetic relationships based on the *E. canis* p28 amino acid sequences are shown in FIG. 12.

Nucleotide sequence and accession numbers. The GenBank accession numbers for the nucleic acid and amino acid sequences for the complete nine gene *E. canis* (Jake strain) p28 gene locus is AF082744. This accession number was originally assigned to p28-7, but has been updated with the sequence of the nine gene p28 locus, which includes p28-7. GenBank accession numbers for nucleic acid and amino acid sequences of p28-7 in other *E. canis* isolates described in this study are: Louisiana, AF082745; Oklahoma, AF082746; Demon, AF082747; DJ, AF082748; Fuzzy, AF082749; Florida, AF082750.

Multiple bands in the 28-kilodalton range have been observed by immunoblots of convalescent sera from *E. canis* infected dogs (Rikihisa et al. 1994), and expression of multiple p28 proteins could be an explanation for this observation. Southern blot studies suggest that other p28 genes, in addition to the five members of this locus, are present in the genome (McBride et al. 1999; Ohfishi et al., 1998b).

In this study a single gene locus containing nine tandemly arranged *E. canis* p28 genes encoding homologous, but nonidentical, p28 genes was identified. The nine gene locus included four new p28 genes (FIGS. 13–16) and five tandemly arranged p28 genes that were reported above. Eight of the p28 genes were located on one DNA strand, and one p28 gene was found on the complementary strand. The nucleic acid homology among the nine p28 gene members was 37 to 75%, and the amino acid homology ranged from 28 to 72%.

The P28s of *E. canis* were found to be as closely related to 28-kilodalton proteins of other species such as *E. chaffeensis* as they are to themselves (McBride et al., 2000). Differences among the proteins are found primarily in several major hypervariable regions and suggest that these regions are surface exposed and subject to selective pressure by the immune system (McBride et al. 2000).

Conservation of an *E. canis* p28 gene (p28-7) among seven geographically different isolates has been reported (McBride et al., 1999), suggesting that *E. canis* may be highly conserved in North America. Similarly, the 120-kDa glycoprotein of *E. canis* is also conserved among, isolates in the United States (Yu et al., 1997). In contrast, both the 120-kDa and the 28-kDa protein genes of *E. chaffeensis* are divergent among isolates (Yu et al., 1999a; Chen et al., 1997). The diversity of the 28-kDa protein gene of *E. chaffeensis* appeared to result from point mutations in the hypervariable regions perhaps due to selective immune pressure (Yu et al., 1999a). These data suggest that *E. canis* may have been introduced into North America relatively recently, and this may account for the conservation that was observed among isolates. The conservation of p28 genes in *E. canis* isolates may provide an opportunity to develop vaccine and serodiagnostic antigens that are particularly effective for disease prevention and serodiagnosis. A mixture of the P28s may provide the most reliable serodiagnostic test, but serodiagnosis with a single P28 has been reported to be useful for immunodiagnosis (Ohashi et al., 1998b; McBride et al., 1999).

The following references were cited herein.
Alleman A. R., et al., (1997) *Infect Immun* 65: 156–163.
Anderson B. E., et al., (1991) *J Clin Microbiol* 29: 2838–2842.
Anderson B. E., et al., (1992) *Int J Syst Bacteriol* 42: 299–302.
Brouqui P., et al., (1992) *J Clin Microbiol* 30: 1062–1066.
Chen S. M., et al., (1997) *Clin Diag Lab Immunol* 4: 731–735.
Chen S. M., et al., (1994) *Am J Trop Med Hyg* 50: 52–58.
Dawson J. E., et al., (1992) *Am J Vet Res* 53: 1322–1327.
Dawson J. E., et al., (1991) *J Infect Dis* 163: 564–567.
Donatien, et al., (1935) *Bull Soc Pathol Exot* 28: 418–9.
Ewing, (1963) *J Am Vet Med Assoc* 143: 503–6.
Groves M. G., et al., (1975) *Am J Vet Res* 36: 937–940.
Harrus S., et al., (1998) *J Clin Microbiol* 36: 73–76.
Jameson B. A., et al., (1988) *CABIOS* 4: 181–186.
Jongejan F., et al., (1993) *Rev Elev Med Vet Pays Trop* 46: 145–152.
McBride J. W., et al., (1996) *J Vet Diag Invest* 8: 441–447.
McBride, et al., (1999) *Clin Diagn Lab Immunol.* 6: 392–399.
McBride, et al., (2000) *Gene*; In press
McClure, (1985) *Ann Rev Biochem* 54: 171–204.
McGeoch D. J. (1985) *Virus Res* 3: 271–286.
Nyindo M., et al., (1991) *Am J Vet Res* 52: 1225–1230.
Nyindo, et al., (1971) *Am J Vet Res* 32: 1651–58.
Ohashi, et al., (1998a) *Infect Immun* 66: 132–9.
Ohashi, et al., (1998b) *J Clin Microb* 36: 2671–80
Reddy, et al., (1998) *Biochem Biophys Res Comm* 247: 636–43.
Rikihisa, et al., (1994) *J Clin Microbiol* 32: 2107–12.
Rothbard J. B., et al., (1988) *The EMBO J* 7: 93–100.
Sambrook J., et al., (1989) *In Molecular Cloning: A Laboratory, Manual.* Cold Spring, Harbor: Cold Spring Harbor Press.
Suisona et al., (1999) *Biochem. Biophys. Res. Commun.* 257: 300–305.
Troy G. C., et al., (1990) Canine ehrlichiosis. In *Infectious diseases of the dog and cat.* Green C. E. (ed). Philidelphia: W. B. Sauders Co.
von Heijne, (1986) *Nucl Acids Res* 14: 4683–90.
Walker, et al. (1970) *J Am Vet Med Assoc* 157: 43–55.
Weiss E., et al., (1975) *Appl Microbiol* 30: 456–463.
Yu et al., (1993) *J. Clin. Microbiol.* 31: 3284–3288.
Yu, et al., (1997) *Gene* 184: 149–154.
Yu, et al., (1999a) *J. Clin. Microbiol.* 37: 1137–1143.
Yu et al., (2000) *Gene* 248: 59–68.

Any patents or publications mentioned in this specification are indicative of the levels of those skilled in the art to which the invention pertains. These patents and publications are herein incorporated by reference to the same extent as if each individual publication was individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary. and are not intended as limitations on the scope of the invention. Changes therein and other uses will occur to those skilled in the art which are encompassed within the spirit of the invention as defined by the scope of the claims.

What is claimed is:

1. A method of inhibiting *Ehrlichia canis* infection in a subject comprising the steps of:
   identifying a subject prior to exposure or suspected of being exposed to or infected with *Ehrlichia canis*; and
   administering a composition comprising a 28-kDa antigen of *Ehrlichia canis* in an amount effective to inhibit *Ehrlichia canis* infection, wherein said 28-kDa antigen comprises amino acid sequence of SEQ ID No. 2.

2. The method of claim 1, wherein said composition is dispersed in a pharmaceutically acceptable carrier.

* * * * *

UNITED STATES PATENT AND TRADEMARK OFFICE
CERTIFICATE OF CORRECTION

PATENT NO. : 6,660,269 B1
DATED : December 9, 2003
INVENTOR(S) : David H. Walker, Xue-Jie Yu and Jere W. McBride It is certified that error appears in the above-identified patent and that said Letters Patent is hereby corrected as shown below:

Column 1,
Line 7, please insert -- of -- between "application" and "Ser. No.".
Lines 9 and 11, please insert -- of -- between "part" and "Ser. No.".

Column 4,
Line 15, "omp" should be italicized.

Column 5,
Line 61, "linkeding" should read -- linking --.

Column 7,
Line 32, please remove "for a".

Column 8,
Line 23, "recombinaintly" should read -- recombinantly --.
Line 33, "comprise" should read -- comprised --.

Column 9,
Line 48, "enerated" should read -- generated --.

Column 12,
Line 6, "Nitucleic" should read -- Nucleic --.
Line 26, "genornic" should read -- genomic --.

Column 13,
Line 26, "alkailine" should read -- alkaline --.
Line 27, "conjuglited" should read -- conjugated --.
Line 33, "to" should read -- To --.
Line 58, "Comparasion" should read -- Comparison --.

Column 16,
Line 58, please insert a period after "7 and 8)".

Column 17,
Line 3, please insert a space after "Regions".
Line 13, "the" should red -- The --.
Line 53, pleae insert a space before "Also disclosed".

UNITED STATES PATENT AND TRADEMARK OFFICE
CERTIFICATE OF CORRECTION

PATENT NO. : 6,660,269 B1
DATED : December 9, 2003
INVENTOR(S) : David H. Walker, Xue-Jie Yu and Jere W. McBride It is certified that error appears in the above-identified patent and that said Letters Patent is hereby corrected as shown below:

Column 20,
Line 61, please delete the comma after "among".

Signed and Sealed this

First Day of June, 2004

JON W. DUDAS
*Acting Director of the United States Patent and Trademark Office*

SEQUENCE LISTING

```
<160> NUMBER OF SEQ ID NOS: 46

<210> SEQ ID NO 1
<211> LENGTH: 1607
<212> TYPE: DNA
<213> ORGANISM: Ehrlichia canis
<220> FEATURE:
<223> OTHER INFORMATION: nucleic acid sequence of E. canis p28-7

<400> SEQUENCE: 1
attttattta ttaccaatct tatataatat attaaatttc tcttacaaaa atctctaatg      60 ttttataccct aatatatata ttctggcttg tatctactt gcacttccac tattgttaat     120
ttattttcac tattttaggt gtaatatgaa ttgcaaaaaa attcttataa caactgcatt     180
aatatcatta atgtactcta ttccaagcat atcttttct gatactatac aagatggtaa     240
catgggtggt aacttctata ttagtggaaa gtatgtacca agtgtctcac attttggtag    300
cttctcagct aaagaagaaa gcaaatcaac tgttggagtt tttggattaa aacatgattg    360
ggatggaagt ccaatactta agaataaaca cgctgacttt actgttccaa actattcgtt    420
cagatacgag aacaatccat ttctagggtt tgcaggagct atcggttact caatgggtgg    480
```

```
cccaagaata gaattcgaaa tatcttatga agcattcgac gtaaaaagtc ctaatatcaa    540
ttatcaaaat gacgcgcaca ggtactgcgc tctatctcat cacacatcgg cagccatgga    600
agctgataaa tttgtcttct taaaaaacga agggttaatt gacatatcac ttgcaataaa    660
tgcatgttat gatataataa atgacaaagt acctgtttct ccttatatat gcgcaggtat    720
tggtactgat tgatttcta tgtttgaagc tacaagtcct aaaatttcct accaaggaaa    780
actgggcatt agttactcta ttaatccgga aacctctgtt ttcatcggtg gcatttcca    840 caggatcata ggtaatgagt ttagagatat tcctgcaata gtacctagta actcaactac    900
aataagtgga ccacaatttg caacagtaac actaaatgtg tgtcactttg gtttagaact    960
tggaggaaga tttaacttct aattttattg ttgccacata ttaaaaatga tctaaacttg   1020
tttttawtat tgctacatac aaaaaaagaa aaatagtggc aaaagaatgt agcaataaga   1080 ggggggggg ggaccaaatt tatcttctat gcttcccaag ttttttcycg ctatttatga   1140
cttaaacaac agaaggtaat atcctcacgg aaaacttatc ttcaaatatt ttatttatta   1200
ccaatcttat ataatatatt aaatttctct tacaaaaatc actagtattt tataccaaaa   1260
tatatattct gacttgcttt tcttctgcac ttctactatt tttaatttat ttgtcactat   1320
taggttataa taawatgaat tgcmaaagat ttttcatagc aagtgcattg atatcactaa   1380
tgtctttctt acctagcgta tcttttttctg aatcaataca tgaagataat ataaatggta   1440
acttttacat tagtgcaaag tatatgccaa gtgcctcaca ctttggcgta ttttcagtta   1500
aagaagagaa aaacacaaca actggagttt tcggattaaa acaagattgg gacggagcaa   1560
cactaaagga tgcaagcwgc agccacacaw tagacccaag tacaatg                1607
```

<210> SEQ ID NO 2
<211> LENGTH: 278
<212> TYPE: PRT
<213> ORGANISM: Ehrlichia canis
<220> FEATURE:
<223> OTHER INFORMATION: amino acid sequence of E. canis p28-7 protein

<400> SEQUENCE: 2

```
Met Asn Cys Lys Lys Ile Leu Ile Thr Thr Ala Leu Ile Ser Leu
                 5                  10                  15

Met Tyr Ser Ile Pro Ser Ile Ser Phe Ser Asp Thr Ile Gln Asp
                20                  25                  30

Gly Asn Met Gly Gly Asn Phe Tyr Ile Ser Gly Lys Tyr Val Pro
                35                  40                  45

Ser Val Ser His Phe Gly Ser Phe Ser Ala Lys Glu Glu Ser Lys
                50                  55                  60

Ser Thr Val Gly Val Phe Gly Leu Lys His Asp trp Asp Gly Ser
                65                  70                  75

Pro Ile Leu Lys Asn Lys His Ala Asp Phe Thr Val Pro Asn Tyr
                80                  85                  90

Ser Phe Arg Tyr Glu Asn Asn Pro Phe Leu Gly Phe Ala Gly Ala
                95                 100                 105

Ile Gly Tyr Ser Met Gly Gly Pro Arg Ile Glu Phe Glu Ile Ser
               110                 115                 120

Tyr Glu Ala Phe Asp Val Lys Ser Pro Asn Ile Asn Tyr Gln Asn
               125                 130                 135

Asp Ala His Arg Tyr Cys Ala Leu Ser His His Thr Ser Ala Ala
               140                 145                 150

Met Glu Ala Asp Lys Phe Val Phe Leu Lys Asn Glu Gly Leu Ile
```

155                 160                 165
Asp Ile Ser Leu Ala Ile Asn Ala Cys Tyr Asp Ile Ile Asn Asp
                170                 175                 180

Lys Val Pro Val Ser Pro Tyr Ile Cys Ala Gly Ile Gly Thr Asp
                185                 190                 195

Leu Ile Ser Met Phe Glu Ala Thr Ser Pro Lys Ile Ser Tyr Gln
                200                 205                 210

Gly Lys Leu Gly Ile Ser Tyr Ser Ile Asn Pro Glu Thr Ser Val
                215                 220                 225

Phe Ile Gly Gly His Phe His Arg Ile Gly Asn Glu Phe Arg
                230                 235                 240

Asp Ile Pro Ala Ile Val Pro Ser Asn Ser Thr Thr Ile Ser Gly
                245                 250                 255

Pro Gln Phe Ala Thr Val Thr Leu Asn Val Cys His Phe Gly Leu
                260                 265                 270

Glu Leu Gly Gly Arg Phe Asn Phe
                275

<210> SEQ ID NO 3
<211> LENGTH: 849
<212> TYPE: DNA
<213> ORGANISM: Ehrlichia canis
<220> FEATURE:
<221> NAME/KEY: mat_peptide
<223> OTHER INFORMATION: nucleic acid sequence of p28-5

<400> SEQUENCE: 3
atgaattgta aaaagttttt cacaataagt gcattgatat catccatata cttcctacct      60
aatgtctcat actctaaccc agtatatggt aacagtatgt atggtaattt ttacatatca    120
ggaaagtaca tgccaagtgt tcctcatttt ggaatttttt cagctgaaga agagaaaaaa    180
aagacaactg tagtatatgg cttaaaagaa aactgggcag gagatgcaat atctagtcaa    240
agtccagatg ataattttac cattcgaaat tactcattca gtatgcaag caacaagttt     300 ttagggtttg cagtagctat tggttactcg ataggcagtc aagaataga agttgagatg     360 tcttatgaag catttgatgt gaaaaatcca ggtgataatt acaaaaacgg tgcttacagg    420
tattgtgctt tatctcatca agatgatgcg gatgatgaca tgactagtgc aactgacaaa    480
tttgtatatt taattaatga aggattactt aacatatcat ttatgacaaa catatgttat    540
gaaacagcaa gcaaaaatat acctctctct ccttacatat gtgcaggtat tggtactgat    600
ttaattcaca tgtttgaaac tacacatcct aaaatttctt atcaaggaaa gctagggttg    660
gcctacttcg taagtgcaga gtcttcggtt tcttttggta tatattttca taaaattata    720
aataataagt ttaaaaatgt tccagccatg gtacctatta actcagacga gatagtagga    780
ccacagtttg caacagtaac attaaatgta tgctactttg gattagaact tggatgtagg    840
ttcaacttc                                                            849

<210> SEQ ID NO 4
<211> LENGTH: 283
<212> TYPE: PRT
<213> ORGANISM: Ehrlichia canis
<220> FEATURE:
<223> OTHER INFORMATION: amino acid sequence of p28-5 protein

<400> SEQUENCE: 4

Met Asn Cys Lys Lys Val Phe Thr Ile Ser Ala Leu Ile Ser Ser
                  5                  10                  15

Ile Tyr Phe Leu Pro Asn Val Ser Tyr Ser Asn Pro Val Tyr Gly
            20                  25                  30

Asn Ser Met Tyr Gly Asn Phe Tyr Ile Ser Gly Lys Tyr Met Pro
            35                  40                  45

Ser Val Pro His Phe Gly Ile Phe Ser Ala Glu Glu Lys Lys
            50                  55                  60

Lys Thr Thr Val Val Tyr Gly Leu Lys Glu Asn Trp Ala Gly Asp
            65                  70                  75

Ala Ile Ser Ser Gln Ser Pro Asp Asp Asn Phe Thr Ile Arg Asn
            80                  85                  90

Tyr Ser Phe Lys Tyr Ala Ser Asn Lys Phe Leu Gly Phe Ala Val
            95                 100                 105

Ala Ile Gly Tyr Ser Ile Gly Ser Pro Arg Ile Glu Val Glu Met
           110                 115                 120

Ser Tyr Glu Ala Phe Asp Val Lys Asn Pro Gly Asp Asn Tyr Lys
           125                 130                 135

Asn Gly Ala Tyr Arg Tyr Cys Ala Leu Ser His Gln Asp Asp Ala
           140                 145                 150

Asp Asp Asp Met Thr Ser Ala Thr Asp Lys Phe Val Tyr Leu Ile
           155                 160                 165

Asn Glu Gly Leu Leu Asn Ile Ser Phe Met Thr Asn Ile Cys Tyr
           170                 175                 180

Glu Thr Ala Ser Lys Asn Ile Pro Leu Ser Pro Tyr Ile Cys Ala
           185                 190                 195

Gly Ile Gly Thr Asp Leu Ile His Met Phe Glu Thr Thr His Pro
           200                 205                 210

Lys Ile Ser Tyr Gln Gly Lys Leu Gly Leu Ala Tyr Phe Val Ser
           215                 220                 225

Ala Glu Ser Ser Val Ser Phe Gly Ile Tyr Phe His Lys Ile Ile
           230                 235                 240

Asn Asn Lys Phe Lys Asn Val Pro Ala Met Val Pro Ile Asn Ser
           245                 250                 255

Asp Glu Ile Val Gly Pro Gln Phe Ala Thr Val Thr Leu Asn Val
           260                 265                 270

Cys Tyr Phe Gly Leu Glu Leu Gly Cys Arg Phe Asn Phe
           275                 280

<210> SEQ ID NO 5
<211> LENGTH: 840
<212> TYPE: DNA
<213> ORGANISM: Ehrlichia canis
<220> FEATURE:
<221> NAME/KEY: mat_peptide
<223> OTHER INFORMATION: nucleic acid sequence of p28-6

<400> SEQUENCE: 5
atgaattgca aaaaaattct tataacaact gcattaatgt cattaatgta ctatgctcca      60
agcatatctt tttctgatac tatacaagac gataacactg gtagcttcta catcagtgga     120
aaatatgtac caagtgtttc acattttggt gttttctcag ctaaagaaga agaaactca     180 actgttggag tttttggatt aaaacatgat tggaatggag gtacaatatc taactcttct     240
ccagaaaata tattcacagt tcaaaattat tcgtttaaat acgaaaacaa cccattctta     300
gggtttgcag gagctattgg ttattcaatg ggtggcccaa gaatagaact tgaagttctg     360
tacgagacat cgatgtgaa aaatcagaac aataattata agaacggcgc acacagatac     420

-continued

```
tgtgctttat ctcatcatag ttcagcaaca agcatgtcct ccgcaagtaa caaatttgtt    480
ttcttaaaaa atgaagggtt aattgactta tcatttatga taaatgcatg ctatgacata    540
ataattgaag gaatgccttt ttcaccttat atttgtgcag gtgttggtac tgatgttgtt    600
tccatgtttg aagctataaa tcctaaaatt tcttaccaag gaaaactagg attaggttat    660
agtataagtt cagaagcctc tgtttttatc ggtggacact ttcacagagt cataggtaat    720
gaatttagag acatccctgc tatggttcct agtggatcaa atcttccaga aaaccaattt    780
gcaatagtaa cactaaatgt gtgtcacttt ggcatagaac ttggaggaag atttaacttc    840

<210> SEQ ID NO 6
<211> LENGTH: 280
<212> TYPE: PRT
<213> ORGANISM: Ehrlichia canis
<220> FEATURE:
<223> OTHER INFORMATION: amino acid sequence of p28-6 protein

<400> SEQUENCE: 6

Met Asn Cys Lys Lys Ile Leu Ile Thr Thr Ala Leu Met Ser Leu
                5                   10                  15

Met Tyr Tyr Ala Pro Ser Ile Ser Phe Ser Asp Thr Ile Gln Asp
                20                  25                  30

Asp Asn Thr Gly Ser Phe Tyr Ile Ser Gly Lys Tyr Val Pro Ser
                35                  40                  45

Val Ser His Phe Gly Val Phe Ser Ala Lys Glu Glu Arg Asn Ser
                50                  55                  60

Thr Val Gly Val Phe Gly Leu Lys His Asp Trp Asn Gly Gly Thr
                65                  70                  75

Ile Ser Asn Ser Ser Pro Glu Asn Ile Phe Thr Val Gln Asn Tyr
                80                  85                  90

Ser Phe Lys Tyr Glu Asn Asn Pro Phe Leu Gly Phe Ala Gly Ala
                95                  100                 105

Ile Gly Tyr Ser Met Gly Gly Pro Arg Ile Glu Leu Glu Val Leu
                110                 115                 120

Tyr Glu Thr Phe Asp Val Lys Asn Gln Asn Asn Asn Tyr Lys Asn
                125                 130                 135

Gly Ala His Arg Tyr Cys Ala Leu Ser His His Ser Ser Ala Thr
                140                 145                 150

Ser Met Ser Ser Ala Ser Asn Lys Phe Val Phe Leu Lys Asn Glu
                155                 160                 165

Gly Leu Ile Asp Leu Ser Phe Met Ile Asn Ala Cys Tyr Asp Ile
                170                 175                 180

Ile Ile Glu Gly Met Pro Phe Ser Pro Tyr Ile Cys Ala Gly Val
                185                 190                 195

Gly Thr Asp Val Val Ser Met Phe Glu Ala Ile Asn Pro Lys Ile
                200                 205                 210

Ser Tyr Gln Gly Lys Leu Gly Leu Gly Tyr Ser Ile Ser Ser Glu
                215                 220                 225

Ala Ser Val Phe Ile Gly Gly His Phe His Arg Val Ile Gly Asn
                230                 235                 240

Glu Phe Arg Asp Ile Pro Ala Met Val Pro Ser Gly Ser Asn Leu
                245                 250                 255

Pro Glu Asn Gln Phe Ala Ile Val Thr Leu Asn Val Cys His Phe
                260                 265                 270
```

```
Gly Ile Glu Leu Gly Gly Arg Phe Asn Phe
                275                 280

<210> SEQ ID NO 7
<211> LENGTH: 133
<212> TYPE: PRT
<213> ORGANISM: Ehrlichia canis
<220> FEATURE:
<223> OTHER INFORMATION: partial amino acid sequence of p28-5 protein

<400> SEQUENCE: 7

Met Asn Cys Lys Lys Val Phe Thr Ile Ser Ala Leu Ile Ser Ser
                 5                  10                  15

Ile Tyr Phe Leu Pro Asn Val Ser Tyr Ser Asn Pro Val Tyr Gly
                20                  25                  30

Asn Ser Met Tyr Gly Asn Phe Tyr Ile Ser Gly Lys Tyr Met Pro
                35                  40                  45

Ser Val Pro His Phe Gly Ile Phe Ser Ala Glu Glu Lys Lys
                50                  55                  60

Lys Thr Thr Val Val Tyr Gly Leu Lys Glu Asn Trp Ala Gly Asp
                65                  70                  75

Ala Ile Ser Ser Gln Ser Pro Asp Asp Asn Phe Thr Ile Arg Asn
                80                  85                  90

Tyr Ser Phe Lys Tyr Ala Ser Asn Lys Phe Leu Gly Phe Ala Val
                95                 100                 105

Ala Ile Gly Tyr Ser Ile Gly Ser Pro Arg Ile Glu Val Glu Met
               110                 115                 120

Ser Tyr Glu Ala Phe Asp Val Lys Asn Gln Gly Asn Asn
               125                 130

<210> SEQ ID NO 8
<211> LENGTH: 287
<212> TYPE: PRT
<213> ORGANISM: Ehrlichia canis
<220> FEATURE:
<223> OTHER INFORMATION: amino acid sequence of p28-4 protien

<400> SEQUENCE: 8

Met Lys Tyr Lys Lys Thr Phe Thr Val Thr Ala Leu Val Leu Leu
                 5                  10                  15

Thr Ser Phe Thr His Phe Ile Pro Phe Tyr Ser Pro Ala Arg Ala
                20                  25                  30

Ser Thr Ile His Asn Phe Tyr Ile Ser Gly Lys Tyr Met Pro Thr
                35                  40                  45

Ala Ser His Phe Gly Ile Phe Ser Ala Lys Glu Glu Gln Ser Phe
                50                  55                  60

Thr Lys Val Leu Val Gly Leu Asp Gln Arg Leu Ser His Asn Ile
                65                  70                  75

Ile Asn Asn Asn Asp Thr Ala Lys Ser Leu Lys Val Gln Asn Tyr
                80                  85                  90

Ser Phe Lys Tyr Lys Asn Asn Pro Phe Leu Gly Phe Ala Gly Ala
                95                 100                 105

Ile Gly Tyr Ser Ile Gly Asn Ser Arg Ile Glu Leu Glu Val Ser
               110                 115                 120

His Glu Ile Phe Asp Thr Lys Asn Pro Gly Asn Asn Tyr Leu Asn
               125                 130                 135

Asp Ser His Lys Tyr Cys Ala Leu Ser His Gly Ser His Ile Cys
               140                 145                 150
```

-continued

```
Ser Asp Gly Asn Ser Gly Asp Trp Tyr Thr Ala Lys Thr Asp Lys
                155                 160                 165

Phe Val Leu Leu Lys Asn Glu Gly Leu Leu Asp Val Ser Phe Met
                170                 175                 180

Leu Asn Ala Cys Tyr Asp Ile Thr Thr Glu Lys Met Pro Phe Ser
                185                 190                 195

Pro Tyr Ile Cys Ala Gly Ile Gly Thr Asp Leu Ile Ser Met Phe
                200                 205                 210

Glu Thr Thr Gln Asn Lys Ile Ser Tyr Gln Gly Lys Leu Gly Leu
                215                 220                 225

Asn Tyr Thr Ile Asn Ser Arg Val Ser Val Phe Ala Gly Gly His
                230                 235                 240

Phe His Lys Val Ile Gly Asn Glu Phe Lys Gly Ile Pro Thr Leu
                245                 250                 255

Leu Pro Asp Gly Ser Asn Ile Lys Val Gln Gln Ser Ala Thr Val
                260                 265                 270

Thr Leu Asp Val Cys His Phe Gly Leu Glu Ile Gly Ser Arg Phe
                275                 280                 285

Phe Phe

<210> SEQ ID NO 9
<211> LENGTH: 281
<212> TYPE: PRT
<213> ORGANISM: Ehrlichia chaffeensis
<220> FEATURE:
<223> OTHER INFORMATION: amino acid sequence of E. chaffeensis P28

<400> SEQUENCE: 9

Met Asn Tyr Lys Lys Val Phe Ile Thr Ser Ala Leu Ile Ser Leu
                5                   10                  15

Ile Ser Ser Leu Pro Gly Val Ser Phe Ser Asp Pro Ala Gly Ser
                20                  25                  30

Gly Ile Asn Gly Asn Phe Tyr Ile Ser Gly Lys Tyr Met Pro Ser
                35                  40                  45

Ala Ser His Phe Gly Val Phe Ser Ala Lys Glu Glu Arg Asn Thr
                50                  55                  60

Thr Val Gly Val Phe Gly Leu Lys Gln Asn Trp Asp Gly Ser Ala
                65                  70                  75

Ile Ser Asn Ser Ser Pro Asn Asp Val Phe Thr Val Ser Asn Tyr
                80                  85                  90

Ser Phe Lys Tyr Glu Asn Asn Pro Phe Leu Gly Phe Ala Gly Ala
                95                  100                 105

Ile Gly Tyr Ser Met Asp Gly Pro Arg Ile Glu Leu Glu Val Ser
                110                 115                  120

Tyr Glu Thr Phe Asp Val Lys Asn Gln Gly Asn Asn Tyr Lys Asn
                125                 130                 135

Glu Ala His Arg Tyr Cys Ala Leu Ser His Asn Ser Ala Ala Asp
                140                 145                 150

Met Ser Ser Ala Ser Asn Asn Phe Val Phe Leu Lys Asn Glu Gly
                155                 160                 165

Leu Leu Asp Ile Ser Phe Met Leu Asn Ala Cys Tyr Asp Val Val
                170                 175                 180

Gly Glu Gly Ile Pro Phe Ser Pro Tyr Ile Cys Ala Gly Ile Gly
                185                 190                 195
```

-continued

Thr Asp Leu Val Ser Met Phe Glu Ala Thr Asn Pro Lys Ile Ser
              200                 205                 210

Tyr Gln Gly Lys Leu Gly Leu Ser Tyr Ser Ile Ser Pro Glu Ala
              215                 220                 225

Ser Val Phe Ile Gly Gly His Phe His Lys Val Ile Gly Asn Glu
              230                 235                 240

Phe Arg Asp Ile Pro Thr Ile Ile Pro Thr Gly Ser Thr Leu Ala
              245                 250                 255

Gly Lys Gly Asn Tyr Pro Ala Ile Val Ile Leu Asp Val Cys His
              260                 265                 270

Phe Gly Ile Glu Leu Gly Gly Arg Phe Ala Phe
              275                 280

<210> SEQ ID NO 10
<211> LENGTH: 283
<212> TYPE: PRT
<213> ORGANISM: Ehrlichia chaffeensis
<220> FEATURE:
<223> OTHER INFORMATION: amino acid sequence of E. chaffeensis OMP-1B

<400> SEQUENCE: 10

Met Asn Tyr Lys Lys Ile Phe Val Ser Ser Ala Leu Ile Ser Leu
              5                   10                  15

Met Ser Ile Leu Pro Tyr Gln Ser Phe Ala Asp Pro Val Thr Ser
              20                  25                  30

Asn Asp Thr Gly Ile Asn Asp Ser Arg Glu Gly Phe Tyr Ile Ser
              35                  40                  45

Val Lys Tyr Asn Pro Ser Ile Ser His Phe Arg Lys Phe Ser Ala
              50                  55                  60

Glu Glu Ala Pro Ile Asn Gly Asn Thr Ser Ile Thr Lys Lys Val
              65                  70                  75

Phe Gly Leu Lys Lys Asp Gly Asp Ile Ala Gln Ser Ala Asn Phe
              80                  85                  90

Asn Arg Thr Asp Pro Ala Leu Glu Phe Gln Asn Asn Leu Ile Ser
              95                  100                 105

Gly Phe Ser Gly Ser Ile Gly Tyr Ala Met Asp Gly Pro Arg Ile
              110                 115                 120

Glu Leu Glu Ala Ala Tyr Gln Lys Phe Asp Ala Lys Asn Pro Asp
              125                 130                 135

Asn Asn Asp Thr Asn Ser Gly Asp Tyr Tyr Lys Tyr Phe Gly Leu
              140                 145                 150

Ser Arg Glu Asp Ala Ile Ala Asp Lys Lys Tyr Val Val Leu Lys
              155                 160                 165

Asn Glu Gly Ile Thr Phe Met Ser Leu Met Val Asn Thr Cys Tyr
              170                 175                 180

Asp Ile Thr Ala Glu Gly Val Pro Phe Ile Pro Tyr Ala Cys Ala
              185                 190                 195

Gly Val Gly Ala Asp Leu Ile Asn Val Phe Lys Asp Phe Asn Leu
              200                 205                 210

Lys Phe Ser Tyr Gln Gly Lys Ile Gly Ile Ser Tyr Pro Ile Thr
              215                 220                 225

Pro Glu Val Ser Ala Phe Ile Gly Gly Tyr Tyr His Gly Val Ile
              230                 235                 240

Gly Asn Asn Phe Asn Lys Ile Pro Val Ile Thr Pro Val Val Leu
              245                 250                 255

```
Glu Gly Ala Pro Gln Thr Thr Ser Ala Leu Val Thr Ile Asp Thr
            260                 265                 270

Gly Tyr Phe Gly Gly Glu Val Gly Val Arg Phe Thr Phe
            275                 280

<210> SEQ ID NO 11
<211> LENGTH: 280
<212> TYPE: PRT
<213> ORGANISM: Ehrlichia chaffeensis
<220> FEATURE:
<223> OTHER INFORMATION: amino acid sequence of E. chaffeensis OMP-1C

<400> SEQUENCE: 11

Met Asn Cys Lys Lys Phe Phe Ile Thr Thr Ala Leu Ala Leu Pro
              5                  10                  15

Met Ser Phe Leu Pro Gly Ile Leu Leu Ser Glu Pro Val Gln Asp
             20                  25                  30

Asp Ser Val Ser Gly Asn Phe Tyr Ile Ser Gly Lys Tyr Met Pro
             35                  40                  45

Ser Ala Ser His Phe Gly Val Phe Ser Ala Lys Glu Glu Lys Asn
             50                  55                  60

Pro Thr Val Ala Leu Tyr Gly Leu Lys Gln Asp Trp Asn Gly Val
             65                  70                  75

Ser Ala Ser Ser His Ala Asp Ala Asp Phe Asn Asn Lys Gly Tyr
             80                  85                  90

Ser Phe Lys Tyr Glu Asn Asn Pro Phe Leu Gly Phe Ala Gly Ala
             95                 100                 105

Ile Gly Tyr Ser Met Gly Gly Pro Arg Ile Glu Phe Glu Val Ser
            110                 115                 120

Tyr Glu Thr Phe Asp Val Lys Asn Gln Gly Gly Asn Tyr Lys Asn
            125                 130                 135

Asp Ala His Arg Tyr Cys Ala Leu Asp Arg Lys Ala Ser Ser Thr
            140                 145                 150

Asn Ala Thr Ala Ser His Tyr Val Leu Leu Lys Asn Glu Gly Leu
            155                 160                 165

Leu Asp Ile Ser Leu Met Leu Asn Ala Cys Tyr Asp Val Val Ser
            170                 175                 180

Glu Gly Ile Pro Phe Ser Pro Tyr Ile Cys Ala Gly Val Gly Thr
            185                 190                 195

Asp Leu Ile Ser Met Phe Glu Ala Ile Asn Pro Lys Ile Ser Tyr
            200                 205                 210

Gln Gly Lys Leu Gly Leu Ser Tyr Ser Ile Asn Pro Glu Ala Ser
            215                 220                 225

Val Phe Val Gly Gly His Phe His Lys Val Ala Gly Asn Glu Phe
            230                 235                 240

Arg Asp Ile Ser Thr Leu Lys Ala Phe Ala Thr Pro Ser Ser Ala
            245                 250                 255

Ala Thr Pro Asp Leu Ala Thr Val Thr Leu Ser Val Cys His Phe
            260                 265                 270

Gly Val Glu Leu Gly Gly Arg Phe Asn Phe
            275                 280

<210> SEQ ID NO 12
<211> LENGTH: 286
<212> TYPE: PRT
<213> ORGANISM: Ehrlichia chaffeensis
<220> FEATURE:
```

```
<223> OTHER INFORMATION: amino acid sequence of E. chaffeensis OMP-1D

<400> SEQUENCE: 12

Met Asn Cys Glu Lys Phe Phe Ile Thr Thr Ala Leu Thr Leu Leu
                 5                  10                  15

Met Ser Phe Leu Pro Gly Ile Ser Leu Ser Asp Pro Val Gln Asp
                20                  25                  30

Asp Asn Ile Ser Gly Asn Phe Tyr Ile Ser Gly Lys Tyr Met Pro
                35                  40                  45

Ser Ala Ser His Phe Gly Val Phe Ser Ala Lys Glu Glu Arg Asn
                50                  55                  60

Thr Thr Val Gly Val Phe Gly Ile Glu Gln Asp Trp Asp Arg Cys
                65                  70                  75

Val Ile Ser Arg Thr Thr Leu Ser Asp Ile Phe Thr Val Pro Asn
                80                  85                  90

Tyr Ser Phe Lys Tyr Glu Asn Asn Leu Phe Ser Gly Phe Ala Gly
                95                  100                 105

Ala Ile Gly Tyr Ser Met Asp Gly Pro Arg Ile Glu Leu Glu Val
                110                 115                 120

Ser Tyr Glu Ala Phe Asp Val Lys Asn Gln Gly Asn Asn Tyr Lys
                125                 130                 135

Asn Glu Ala His Arg Tyr Tyr Ala Leu Ser His Leu Leu Gly Thr
                140                 145                 150

Glu Thr Gln Ile Asp Gly Ala Gly Ser Ala Ser Val Phe Leu Ile
                155                 160                 165

Asn Glu Gly Leu Leu Asp Lys Ser Phe Met Leu Asn Ala Cys Tyr
                170                 175                 180

Asp Val Ile Ser Glu Gly Ile Pro Phe Ser Pro Tyr Ile Cys Ala
                185                 190                 195

Gly Ile Gly Ile Asp Leu Val Ser Met Phe Glu Ala Ile Asn Pro
                200                 205                 210

Lys Ile Ser Tyr Gln Gly Lys Leu Gly Leu Ser Tyr Pro Ile Ser
                215                 220                 225

Pro Glu Ala Ser Val Phe Ile Gly Gly His Phe His Lys Val Ile
                230                 235                 240

Gly Asn Glu Phe Arg Asp Ile Pro Thr Met Ile Pro Ser Glu Ser
                245                 250                 255

Ala Leu Ala Gly Lys Gly Asn Tyr Pro Ala Ile Val Thr Leu Asp
                260                 265                 270

Val Phe Tyr Phe Gly Ile Glu Leu Gly Gly Arg Phe Asn Phe Gln
                275                 280                 285

Leu

<210> SEQ ID NO 13
<211> LENGTH: 278
<212> TYPE: PRT
<213> ORGANISM: Ehrlichia chaffeensis
<220> FEATURE:
<223> OTHER INFORMATION: amino acid sequence of E. chaffeensis OMP-1E

<400> SEQUENCE: 13

Met Asn Cys Lys Lys Phe Phe Ile Thr Thr Ala Leu Val Ser Leu
                 5                  10                  15

Met Ser Phe Leu Pro Gly Ile Ser Phe Ser Asp Pro Val Gln Gly
                20                  25                  30
```

```
Asp Asn Ile Ser Gly Asn Phe Tyr Val Ser Gly Lys Tyr Met Pro
                35                  40                  45

Ser Ala Ser His Phe Gly Met Phe Ser Ala Lys Glu Glu Lys Asn
                50                  55                  60

Pro Thr Val Ala Leu Tyr Gly Leu Lys Gln Asp Trp Glu Gly Ile
                65                  70                  75

Ser Ser Ser Ser His Asn Asp Asn His Phe Asn Asn Lys Gly Tyr
                80                  85                  90

Ser Phe Lys Tyr Glu Asn Asn Pro Phe Leu Gly Phe Ala Gly Ala
                95                 100                 105

Ile Gly Tyr Ser Met Gly Gly Pro Arg Val Glu Phe Glu Val Ser
               110                 115                 120

Tyr Glu Thr Phe Asp Val Lys Asn Gln Gly Asn Asn Tyr Lys Asn
               125                 130                 135

Asp Ala His Arg Tyr Cys Ala Leu Gly Gln Gln Asp Asn Ser Gly
               140                 145                 150

Ile Pro Lys Thr Ser Lys Tyr Val Leu Leu Lys Ser Glu Gly Leu
               155                 160                 165

Leu Asp Ile Ser Phe Met Leu Asn Ala Cys Tyr Asp Ile Ile Asn
               170                 175                 180

Glu Ser Ile Pro Leu Ser Pro Tyr Ile Cys Ala Gly Val Gly Thr
               185                 190                 195

Asp Leu Ile Ser Met Phe Glu Ala Thr Asn Pro Lys Ile Ser Tyr
               200                 205                 210

Gln Gly Lys Leu Gly Leu Ser Tyr Ser Ile Asn Pro Glu Ala Ser
               215                 220                 225

Val Phe Ile Gly Gly His Phe His Lys Val Ile Gly Asn Glu Phe
               230                 235                 240

Arg Asp Ile Pro Thr Leu Lys Ala Phe Val Thr Ser Ser Ala Thr
               245                 250                 255

Pro Asp Leu Ala Ile Val Thr Leu Ser Val Cys His Phe Gly Ile
               260                 265                 270

Glu Leu Gly Gly Arg Phe Asn Phe
               275

<210> SEQ ID NO 14
<211> LENGTH: 280
<212> TYPE: PRT
<213> ORGANISM: Ehrlichia chaffeensis
<220> FEATURE:
<223> OTHER INFORMATION: amino acid sequence of E. chaffeensis OMP-1F

<400> SEQUENCE: 14

Met Asn Cys Lys Lys Phe Phe Ile Thr Thr Thr Leu Val Ser Leu
                 5                  10                  15

Met Ser Phe Leu Pro Gly Ile Ser Phe Ser Asp Ala Val Gln Asn
                20                  25                  30

Asp Asn Val Gly Gly Asn Phe Tyr Ile Ser Gly Lys Tyr Val Pro
                35                  40                  45

Ser Val Ser His Phe Gly Val Phe Ser Ala Lys Gln Glu Arg Asn
                50                  55                  60

Thr Thr Thr Gly Val Phe Gly Leu Lys Gln Asp Trp Asp Gly Ser
                65                  70                  75

Thr Ile Ser Lys Asn Ser Pro Glu Asn Thr Phe Asn Val Pro Asn
                80                  85                  90
```

-continued

Tyr Ser Phe Lys Tyr Glu Asn Asn Pro Phe Leu Gly Phe Ala Gly
                95                  100                 105

Ala Val Gly Tyr Leu Met Asn Gly Pro Arg Ile Glu Leu Glu Met
            110                 115                 120

Ser Tyr Glu Thr Phe Asp Val Lys Asn Gln Gly Asn Asn Tyr Lys
            125                 130                 135

Asn Asp Ala His Lys Tyr Tyr Ala Leu Thr His Asn Ser Gly Gly
            140                 145                 150

Lys Leu Ser Asn Ala Gly Asp Lys Phe Val Phe Leu Lys Asn Glu
            155                 160                 165

Gly Leu Leu Asp Ile Ser Leu Met Leu Asn Ala Cys Tyr Asp Val
            170                 175                 180

Ile Ser Glu Gly Ile Pro Phe Ser Pro Tyr Ile Cys Ala Gly Val
            185                 190                 195

Gly Thr Asp Leu Ile Ser Met Phe Glu Ala Ile Asn Pro Lys Ile
            200                 205                 210

Ser Tyr Gln Gly Lys Leu Gly Leu Ser Tyr Ser Ile Ser Pro Glu
            215                 220                 225

Ala Ser Val Phe Val Gly Gly His Phe Lys Val Ile Gly Asn
            230                 235                 240

Glu Phe Arg Asp Ile Pro Ala Met Ile Pro Ser Thr Ser Thr Leu
            245                 250                 255

Thr Gly Asn His Phe Thr Ile Val Thr Leu Ser Val Cys His Phe
            260                 265                 270

Gly Val Glu Leu Gly Gly Arg Phe Asn Phe
            275                 280

<210> SEQ ID NO 15
<211> LENGTH: 284
<212> TYPE: PRT
<213> ORGANISM: Cowdria ruminantium
<220> FEATURE:
<223> OTHER INFORMATION: amino acid sequence of C. ruminantium MAP-1

<400> SEQUENCE: 15

Met Asn Cys Lys Lys Ile Phe Ile Thr Ser Thr Leu Ile Ser Leu
            5                   10                  15

Val Ser Phe Leu Pro Gly Val Ser Phe Ser Asp Val Ile Gln Glu
            20                  25                  30

Glu Asn Asn Pro Val Gly Ser Val Tyr Ile Ser Ala Lys Tyr Met
            35                  40                  45

Pro Thr Ala Ser His Phe Gly Lys Met Ser Ile Lys Glu Asp Ser
            50                  55                  60

Arg Asp Thr Lys Ala Val Phe Gly Leu Lys Lys Asp Trp Asp Gly
            65                  70                  75

Val Lys Thr Pro Ser Gly Asn Thr Asn Ser Ile Phe Thr Glu Lys
            80                  85                  90

Asp Tyr Ser Phe Lys Tyr Glu Asn Asn Pro Phe Leu Gly Phe Ala
            95                  100                 105

Gly Ala Val Gly Tyr Ser Met Asn Gly Pro Arg Ile Glu Phe Glu
            110                 115                 120

Val Ser Tyr Glu Thr Phe Asp Val Arg Asn Pro Gly Gly Asn Tyr
            125                 130                 135

Lys Asn Asp Ala His Met Tyr Cys Ala Leu Asp Thr Ala Ser Ser
            140                 145                 150

```
Ser Thr Ala Gly Ala Thr Thr Ser Val Met Val Lys Asn Glu Asn
                155                 160                 165

Leu Thr Asp Ile Ser Leu Met Leu Asn Ala Cys Tyr Asp Ile Met
                170                 175                 180

Leu Asp Gly Met Pro Val Ser Pro Tyr Val Cys Ala Gly Ile Gly
                185                 190                 195

Thr Asp Leu Val Ser Val Ile Asn Ala Thr Asn Pro Lys Leu Ser
                200                 205                 210

Tyr Gln Gly Lys Leu Gly Ile Ser Tyr Ser Ile Asn Pro Glu Ala
                215                 220                 225

Ser Ile Phe Ile Gly Gly His Phe His Arg Val Ile Gly Asn Glu
                230                 235                 240

Phe Lys Asp Ile Ala Thr Ser Lys Val Phe Thr Ser Ser Gly Asn
                245                 250                 255

Ala Ser Ser Ala Val Ser Pro Gly Phe Ala Ser Ala Ile Leu Asp
                260                 265                 270

Val Cys His Phe Gly Ile Glu Ile Gly Gly Arg Phe Val Phe
                275                 280
```

<210> SEQ ID NO 16
<211> LENGTH: 20
<212> TYPE: DNA
<213> ORGANISM: artificial sequence
<220> FEATURE:
<221> NAME/KEY: primer_bind
<222> LOCATION: nucleotides 313-332 of C. ruminantium MAP-1,
      also nucleotides 307-326 of E. chaffeensis P28
<223> OTHER INFORMATION: forward primer 793 for PCR

<400> SEQUENCE: 16
gcaggagctg ttggttactc                                             20

<210> SEQ ID NO 17
<211> LENGTH: 21
<212> TYPE: DNA
<213> ORGANISM: artificial sequence
<220> FEATURE:
<221> NAME/KEY: primer_bind
<222> LOCATION: nucleotides 823-843 of C. ruminantium MAP-1,
      also nucleotides 814-834 of E. chaffeensis P28
<223> OTHER INFORMATION: reverse primer 1330 for PCR

<400> SEQUENCE: 17
ccttcctcca agttctatgc c                                           21

<210> SEQ ID NO 18
<211> LENGTH: 24
<212> TYPE: DNA
<213> ORGANISM: artificial sequence
<220> FEATURE:
<221> NAME/KEY: primer_bind
<223> OTHER INFORMATION: primer 46f, specific for p28-5 gene

<400> SEQUENCE: 18
atatacttcc tacctaatgt ctca                                        24

<210> SEQ ID NO 19
<211> LENGTH: 20
<212> TYPE: DNA
<213> ORGANISM: artificial sequence
<220> FEATURE:
<221> NAME/KEY: primer_bind
<223> OTHER INFORMATION: primer used for sequencing 28-kDa protein
      genes in E. canis

<400> SEQUENCE: 19
agtgcagagt cttcggtttc                                               20

<210> SEQ ID NO 20
<211> LENGTH: 18
<212> TYPE: DNA
<213> ORGANISM: artificial sequence
<220> FEATURE:
<221> NAME/KEY: primer_bind
<223> OTHER INFORMATION: primer used for sequencing 28-kDa protein
      genes in E. canis

<400> SEQUENCE: 20
gttacttgcg gaggacat                                                 18

<210> SEQ ID NO 21
<211> LENGTH: 24
<212> TYPE: DNA
<213> ORGANISM: artificial sequence
<220> FEATURE:
<221> NAME/KEY: primer_bind
<222> LOCATION: nucleotides 687-710 of E. canis p28-7
<223> OTHER INFORMATION: primer 394 for PCR

<400> SEQUENCE: 21
gcatttccac aggatcatag gtaa                                          24

<210> SEQ ID NO 22
<211> LENGTH: 24
<212> TYPE: DNA
<213> ORGANISM: artificial sequence
<220> FEATURE:
<221> NAME/KEY: primer_bind
<222> LOCATION: nucleotides 710-687 of E. canis p28-7
<223> OTHER INFORMATION: primer 394C for PCR

<400> SEQUENCE: 22
ttacctatga tcctgtggaa atgc                                          24

<210> SEQ ID NO 23
<211> LENGTH: 20
<212> TYPE: DNA
<213> ORGANISM: artificial sequence
<220> FEATURE:
<221> NAME/KEY: primer_bind
<223> OTHER INFORMATION: primer 793C which anneals to a region with E.
      canis p28-7, used to amplify the intergenic region between gene
      p28-6 and p28-7

<400> SEQUENCE: 23
gagtaaccaa cagctcctgc                                               20

<210> SEQ ID NO 24
<211> LENGTH: 24
<212> TYPE: DNA
<213> ORGANISM: artificial sequence
<220> FEATURE:
<221> NAME/KEY: primer_bind
<222> LOCATION:
<223> OTHER INFORMATION: primer EC28OM-F complementary to noncoding
      regions adjacent to the open reading frame of p28-7

<400> SEQUENCE: 24
tctactttgc acttccacta ttgt                                          24

<210> SEQ ID NO 25

```
<211> LENGTH: 24
<212> TYPE: DNA
<213> ORGANISM: artificial sequence
<220> FEATURE:
<221> NAME/KEY: primer_bind
<222> LOCATION:
<223> OTHER INFORMATION: primer EC28OM-R complementary to noncoding
      regions adjacent to the open reading frame of p28-7

<400> SEQUENCE: 25
attcttttgc cactattttt cttt                                            24

<210> SEQ ID NO 26
<211> LENGTH: 25
<212> TYPE: DNA
<213> ORGANISM: artificial sequence
<220> FEATURE:
<221> NAME/KEY: primer_bind
<223> OTHER INFORMATION: primer ECaSA3-2 corresponding to regions within
      p28-6, used to amplify the intergenic region NC3 between gene
      p28-6 and p28-7

<400> SEQUENCE: 26
ctaggattag gttatagtat aagtt                                           25

<210> SEQ ID NO 27
<211> LENGTH: 23
<212> TYPE: PRT
<213> ORGANISM: Ehrlichia canis
<220> FEATURE:
<221> NAME/KEY: PEPTIDE
<223> OTHER INFORMATION: a predicted N-terminal signal peptide of p28-7
      and p28-6

<400> SEQUENCE: 27

Met Asn Cys Lys Lys Ile Leu Ile Thr Thr Ala Leu Met Ser Leu
                 5                  10                  15

Met Tyr Tyr Ala Pro Ser Ile Ser
                 20

<210> SEQ ID NO 28
<211> LENGTH: 25
<212> TYPE: PRT
<213> ORGANISM: Ehrlichia chaffeensis
<220> FEATURE:
<223> OTHER INFORMATION: amino acid sequence of N-terminal signal
      peptide of E. chaffeensis P28

<400> SEQUENCE: 28

Met Asn Tyr Lys Lys Ile Leu Ile Thr Ser Ala Leu Ile Ser Leu
                 5                  10                  15

Ile Ser Ser Leu Pro Gly Val Ser Phe Ser
                 20                  25

<210> SEQ ID NO 29
<211> LENGTH: 26
<212> TYPE: PRT
<213> ORGANISM: Ehrlichia canis
<220> FEATURE:
<223> OTHER INFORMATION: amino acid sequence of putative cleavage site
      of p28-7

<400> SEQUENCE: 29

Met Asn Cys Lys Lys Ile Leu Ile Thr Thr Ala Leu Ile Ser Leu
                 5                  10                  15

Met Tyr Ser Ile Pro Ser Ile Ser Ser Phe Ser
                 20                  25
```

<210> SEQ ID NO 30
<211> LENGTH: 299
<212> TYPE: DNA
<213> ORGANISM: Ehrlichia canis
<220> FEATURE:
<223> OTHER INFORMATION: nucleic acid sequence of intergenic noncoding
      region 1 (28NC1)

<400> SEQUENCE: 30
taatacttct attgtacatg ttaaaaatag tactagtttg cttctgtggt ttataaacgc     60
aagagagaaa tagttagtaa taaattagaa agttaaatat tagaaaagtc atatgttttt    120
cattgtcatt gatactcaac taaaagtagt ataaatgtta cttattaata attttacgta    180
gtatattaaa tttcccttac aaaagccact agtattttat actaaaagct atactttggc    240
ttgtatttaa tttgtatttt tactactgtt aatttacttt cactgtttct ggtgtaaat     299

<210> SEQ ID NO 31
<211> LENGTH: 345
<212> TYPE: DNA
<213> ORGANISM: Ehrlichia canis
<220> FEATURE:
<223> OTHER INFORMATION: nucleic acid sequence of intergenic noncoding
      region 2 (28NC2)

<400> SEQUENCE: 31
taatttcgtg gtacacatat cacgaagcta aaattgttttt tttatctctg ctgtatacaa    60
gagaaaaaat agtagtgaaa attacctaac aatatgacag tacaagttta ccaagcttat   120
tctcacaaaa cttcttgtgt ctttttatctc tttacaatga aatgtacact tagcttcact   180
actgtagagt gtgttttatca atgctttgtt tattaatact ctacataata tgttaaattt    240
ttcttacaaa actcactagt aatttatact agaatatata ttctgacttg tatttgcttt   300
atacttccac tattgttaat ttatttcac tattttaggt gtaat                    345

<210> SEQ ID NO 32
<211> LENGTH: 345
<212> TYPE: DNA
<213> ORGANISM: Ehrlichia canis
<220> FEATURE:
<223> OTHER INFORMATION: nucleic acid sequence of intergenic noncoding
      region 3 (28NC3)

<400> SEQUENCE: 32
tgattttatt gttgccacat attaaaaatg atctaaactt gttttttatta ttgctacata    60 caaaaaaaag aaaaatagtg gcaaaagaat gtagcaataa gagggggggg ggggactaaa   120
tttaccttct attcttctaa tattctttac tatattcaaa tagcacaact caatgcttcc   180
aggaaaatat gtttctaata ttttatttat taccaatcct tatataatat attaaatttc    240
tcttacaaaa atctctaatg ttttatactt aatatatata ttctggcttg tatttacttt   300
gcacttccac tattgttaat ttattttcac tattttaggt gtaat                   345

<210> SEQ ID NO 33
<211> LENGTH: 355
<212> TYPE: DNA
<213> ORGANISM: Ehrlichia canis
<220> FEATURE:
<223> OTHER INFORMATION: nucleic acid sequence of intergenic noncoding
      region 4 (28NC4)

<400> SEQUENCE: 33

-continued

| | |
|---|---|
| taattttatt gttgccacat attaaaaatg atctaaactt gttttawta ttgctacata | 60 |
| caaaaaaga aaaatagtgg caaaagaatg tagcaataag agggggggggg gggaccaaat | 120 |
| ttatcttcta tgcttcccaa gttttttcyc gctatttatg acttaaacaa cagaaggtaa | 180 |
| tatcctcacg gaaaacttat cttcaaatat tttatttatt accaatctta tataatatat | 240 |
| taaatttctc ttacaaaaat cactagtatt ttataccaaa atatatattc tgacttgctt | 300 |
| ttcttctgca cttctactat ttttaattta tttgtcacta ttaggttata ataaw | 355 |

<210> SEQ ID NO 34
<211> LENGTH: 24
<212> TYPE: DNA
<213> ORGANISM: artificial sequence
<220> FEATURE:
<223> OTHER INFORMATION: primer p28-5-818f

<400> SEQUENCE: 34
ttaaacatat gccacttcgg acta                                        24

<210> SEQ ID NO 35
<211> LENGTH: 28
<212> TYPE: DNA
<213> ORGANISM: artificial sequence
<220> FEATURE:
<223> OTHER INFORMATION: primer 1191

<400> SEQUENCE: 35
tatgatcgtg taaaattgct gtgagtat                                    28

<210> SEQ ID NO 36
<211> LENGTH: 20
<212> TYPE: DNA
<213> ORGANISM: artificial sequence
<220> FEATURE:
<223> OTHER INFORMATION: primer ECa28-75C

<400> SEQUENCE: 36
tactggcacg tgctggacta                                             20

<210> SEQ ID NO 37
<211> LENGTH: 22
<212> TYPE: DNA
<213> ORGANISM: artificial sequence
<220> FEATURE:
<223> OTHER INFORMATION: primer ECa5'-1600

<400> SEQUENCE: 37
caccaataaa tgcagagact tc                                          22

<210> SEQ ID NO 38
<211> LENGTH: 26
<212> TYPE: DNA
<213> ORGANISM: artificial sequence
<220> FEATURE:
<223> OTHER INFORMATION: primer 3125

<400> SEQUENCE: 38
aatccatcat ttctcattac agtgtg                                      26

<210> SEQ ID NO 39
<211> LENGTH: 879
<212> TYPE: DNA
<213> ORGANISM: Ehrlichia canis
<220> FEATURE:
<223> OTHER INFORMATION: nucleic acid sequence of E. canis p28-1

<400> SEQUENCE: 39

```
atgaataata aactcaaatt tactataata aacacagtat tagtatgctt attgtcatta      60
cctaatatat cttcctcaaa ggccataaac aataacgcta aaaagtacta cggattatat     120
atcagtggac aatataaacc cagtgtttct gttttcagta attttcagt taaagaaacc     180
aatgtcataa ctaaaaacct tatagcttta aaaaagatg ttgactctat tgaaaccaag     240
actgatgcca gtgtaggtat tagtaaccca tcaaattta ctatcccta tacagctgta     300
tttcaagata attctgtcaa tttcaatgga actattggtt acacctttgc tgaaggtaca     360
agagttgaaa tagaaggttc ttatgaggaa tttgatgtta aaaaccctgg aggctataca     420
ctaagtgatg cctatcgcta ttttgcatta gcacgtgaaa tgaaaggtaa tagttttaca     480
cctaaagaaa aagtttctaa tagtattttt cacactgtaa tgagaaatga tggattatct     540
ataatatctg ttatagtaaa tgtttgctac gatttctctt tgaacaattt gtcaatatcg     600
ccttacatat gtggaggagc agggtagat gctatagaat tcttcgatgt attacacatt     660
aagtttgcat atcaaagcaa gctaggtatt gcttattctc taccatctaa cattagtctc     720
tttgctagtt tatattacca taagtaatg ggcaatcaat ttaaaattt aaatgtccaa     780
catgttgctg aacttgcaag tatacctaaa attacatccg cagttgctac acttaatatt     840
ggttattttg gaggtgaaat tggtgcaaga ttgacatt                             879
```

<210> SEQ ID NO 40
<211> LENGTH: 293
<212> TYPE: PRT
<213> ORGANISM: Ehrlichia canis
<220> FEATURE:
<223> OTHER INFORMATION: amino acid sequence of E. canis p28-1 protein

<400> SEQUENCE: 40

```
Met Asn Asn Lys Leu Lys Phe Thr Ile Ile Asn Thr Val Leu Val
                 5                  10                  15
Cys Leu Leu Ser Leu Pro Asn Ile Ser Ser Lys Ala Ile Asn
             20                  25                  30
Asn Asn Ala Lys Lys Tyr Tyr Gly Leu Tyr Ile Ser Gly Gln Tyr
             35                  40                  45
Lys Pro Ser Val Ser Val Phe Ser Asn Phe Ser Val Lys Glu Thr
             50                  55                  60
Asn Val Ile Thr Lys Asn Leu Ile Ala Leu Lys Lys Asp Val Asp
             65                  70                  75
Ser Ile Glu Thr Lys Thr Asp Ala Ser Val Gly Ile Ser Asn Pro
             80                  85                  90
Ser Asn Phe Thr Ile Pro Tyr Thr Ala Val Phe Gln Asp Asn Ser
             95                 100                 105
Val Asn Phe Asn Gly Thr Ile Gly Tyr Thr Phe Ala Glu Gly Thr
            110                 115                 120
Arg Val Glu Ile Glu Gly Ser Tyr Glu Glu Phe Asp Val Lys Asn
            125                 130                 135
Pro Gly Gly Tyr Thr Leu Ser Asp Ala Tyr Arg Tyr Phe Ala Leu
            140                 145                 150
Ala Arg Glu Met Lys Gly Asn Ser Phe Thr Pro Lys Glu Lys Val
            155                 160                 165
Ser Asn Ser Ile Phe His Thr Val Met Arg Asn Asp Gly Leu Ser
            170                 175                 180
```

```
Ile Ile Ser Val Ile Val Asn Val Cys Tyr Asp Phe Ser Leu Asn
                185                 190                 195

Asn Leu Ser Ile Ser Pro Tyr Ile Cys Gly Gly Ala Gly Val Asp
                200                 205                 210

Ala Ile Glu Phe Phe Asp Val Leu His Ile Lys Phe Ala Tyr Gln
                215                 220                 225

Ser Lys Leu Gly Ile Ala Tyr Ser Leu Pro Ser Asn Ile Ser Leu
                230                 235                 240

Phe Ala Ser Leu Tyr Tyr His Lys Val Met Gly Asn Gln Phe Lys
                245                 250                 255

Asn Leu Asn Val Gln His Val Ala Glu Leu Ala Ser Ile Pro Lys
                260                 265                 270

Ile Thr Ser Ala Val Ala Thr Leu Asn Ile Gly Tyr Phe Gly Gly
                275                 280                 285

Glu Ile Gly Ala Arg Leu Thr Phe
                290         293

<210> SEQ ID NO 41
<211> LENGTH: 840
<212> TYPE: DNA
<213> ORGANISM: Ehrlichia canis
<220> FEATURE:
<223> OTHER INFORMATION: nucleic acid sequence of E. canis p28-2

<400> SEQUENCE: 41
atgaattata agaaaattct agtaagaagc gcgttaatct cattaatgtc aatcttacca     60
tatcagtctt ttgcagatcc tgtaggttca agaactaatg ataacaaaga aggcttctac    120
attagtgcaa agtacaatcc aagtatatca cactttagaa aattctctgc tgaagaaact    180
cctattaatg gaacaaattc tctcactaaa aaagttttcg gactaaagaa agatggtgat    240
ataacaaaaa aagacgattt tacaagagta gctccaggca ttgattttca aaataactta    300
atatcaggat tttcaggaag tattggttac tctatggacg gaccaagaat agaacttgaa    360
gctgcatatc aacaatttaa tccaaaaaac accgataaca atgatactga taatggtgaa    420
tactataaac attttgcatt atctcgtaaa gatgcaatgg aagatcagca atatgtagta    480
cttaaaaatg acggcataac ttttatgtca ttgatggtta atacttgcta tgacattaca    540
gctgaaggag tatctttcgt accatatgca tgtgcaggta taggagcaga tcttatcact    600
atttttaaag acctcaatct aaaatttgct taccaaggaa aaataggtat tagttaccct    660
atcacaccag aagtctctgc atttattggt ggatactacc atggcgttat tggtaataaa    720
tttgagaaga tacctgtaat aactcctgta gtattaaatg atgctcctca aaccacatct    780
gcttcagtaa ctcttgacgt tggatacttt ggcggagaaa ttggaatgag gttcaccttc    840

<210> SEQ ID NO 42
<211> LENGTH: 280
<212> TYPE: PRT
<213> ORGANISM: Ehrlichia canis
<220> FEATURE:
<223> OTHER INFORMATION: amino acid sequence of E. canis p28-2 protein

<400> SEQUENCE: 42

Met Asn Tyr Lys Lys Ile Leu Val Arg Ser Ala Leu Ile Ser Leu
                5                   10                  15

Met Ser Ile Leu Pro Tyr Gln Ser Phe Ala Asp Pro Val Gly Ser
                20                  25                  30

Arg Thr Asn Asp Asn Lys Glu Gly Phe Tyr Ile Ser Ala Lys Tyr
```

|     |     |     |     | 35  |     |     |     |     | 40  |     |     |     |     | 45  |
| --- | --- | --- | --- | --- | --- | --- | --- | --- | --- | --- | --- | --- | --- | --- |

Asn Pro Ser Ile Ser His Phe Arg Lys Phe Ser Ala Glu Glu Thr
     50       55       60

Pro Ile Asn Gly Thr Asn Ser Leu Thr Lys Lys Val Phe Gly Leu
     65       70       75

Lys Lys Asp Gly Asp Ile Thr Lys Lys Asp Asp Phe Thr Arg Val
     80       85       90

Ala Pro Gly Ile Asp Phe Gln Asn Asn Leu Ile Ser Gly Phe Ser
     95       100      105

Gly Ser Ile Gly Tyr Ser Met Asp Gly Pro Arg Ile Glu Leu Glu
     110      115      120

Ala Ala Tyr Gln Gln Phe Asn Pro Lys Asn Thr Asp Asn Asn Asp
     125      130      135

Thr Asp Asn Gly Glu Tyr Tyr Lys His Phe Ala Leu Ser Arg Lys
     140      145      150

Asp Ala Met Glu Asp Gln Gln Tyr Val Val Leu Lys Asn Asp Gly
     155      160      165

Ile Thr Phe Met Ser Leu Met Val Asn Thr Cys Tyr Asp Ile Thr
     170      175      180

Ala Glu Gly Val Ser Phe Val Pro Tyr Ala Cys Ala Gly Ile Gly
     185      190      195

Ala Asp Leu Ile Thr Ile Phe Lys Asp Leu Asn Leu Lys Phe Ala
     200      205      210

Tyr Gln Gly Lys Ile Gly Ile Ser Tyr Pro Ile Thr Pro Glu Val
     215      220      225

Ser Ala Phe Ile Gly Gly Tyr Tyr His Gly Val Ile Gly Asn Lys
     230      235      240

Phe Glu Lys Ile Pro Val Ile Thr Pro Val Val Leu Asn Asp Ala
     245      250      255

Pro Gln Thr Thr Ser Ala Ser Val Thr Leu Asp Val Gly Tyr Phe
     260      265      270

Gly Gly Glu Ile Gly Met Arg Phe Thr Phe
     275      280

<210> SEQ ID NO 43
<211> LENGTH: 828
<212> TYPE: DNA
<213> ORGANISM: Ehrlichia canis
<220> FEATURE:
<223> OTHER INFORMATION: nucleic acid sequence of E. canis p28-3

<400> SEQUENCE: 43

| | | | | | |
|---|---|---|---|---|---|
| atgaactgta | aaaaattct | tataacaact | acattggtat | cactaacaat | tcttttacct | 60 |
| ggcatatctt | tctccaaacc | aatacatgaa | acaatacta | caggaaactt | ttacattatt | 120 |
| ggaaaatatg | taccaagtat | ttcacatttt | gggaacttttt | cagctaaaga | agaaaaaaac | 180 |
| acaacaactg | gaattttttgg | attaaaagaa | tcatggactg | gtggtatcat | ccttgataaa | 240 |
| gaacatgcag | cttttaatat | cccaaattat | tcatttaaat | atgaaaataa | tccatttta | 300 |
| ggatttgcag | gggtaattgg | ctattcaata | ggtagtccaa | gatagaatt | tgaagtatca | 360 |
| tacgagacat | tcgatgtaca | aaatccagga | gataagttta | caatgatgc | acataagtat | 420 |
| tgtgctttat | ccaatgattc | cagtaaaaca | atgaaaagtg | gtaaattcgt | ttttctcaaa | 480 |
| aatgaaggat | taagtgacat | atcactcatg | ttaaatgtat | gttatgatat | aataaacaaa | 540 |
| agaatgcctt | tttcacctta | catatgtgca | ggcattggta | ctgacttaat | attcatgttt | 600 |

```
gacgctataaa accataaagc tgcttatcaa ggaaaattag gttttaatta tccaataagc      660
ccagaagcta acatttctat gggtgtgcac tttcacaaag taacaaacaa cgagtttaga      720
gttcctgttc tattaactgc tggaggactc gctccagata atctatttgc aatagtaaag      780
ttgagtatat gtcattttgg gttagaattt gggtacaggg tcagtttt                   828
```

<210> SEQ ID NO 44
<211> LENGTH: 276
<212> TYPE: PRT
<213> ORGANISM: Ehrlichia canis
<220> FEATURE:
<223> OTHER INFORMATION: amino acid sequence of E. canis p28-3 protein

<400> SEQUENCE: 44

```
Met Asn Cys Lys Lys Ile Leu Ile Thr Thr Thr Leu Val Ser Leu
                 5                  10                  15

Thr Ile Leu Leu Pro Gly Ile Ser Phe Ser Lys Pro Ile His Glu
                20                  25                  30

Asn Asn Thr Thr Gly Asn Phe Tyr Ile Ile Gly Lys Tyr Val Pro
                35                  40                  45

Ser Ile Ser His Phe Gly Asn Phe Ser Ala Lys Glu Glu Lys Asn
                50                  55                  60

Thr Thr Thr Gly Ile Phe Gly Leu Lys Glu Ser Trp Thr Gly Gly
                65                  70                  75

Ile Ile Leu Asp Lys Glu His Ala Ala Phe Asn Ile Pro Asn Tyr
                80                  85                  90

Ser Phe Lys Tyr Glu Asn Asn Pro Phe Leu Gly Phe Ala Gly Val
                95                 100                 105

Ile Gly Tyr Ser Ile Gly Ser Pro Arg Ile Glu Phe Glu Val Ser
               110                 115                 120

Tyr Glu Thr Phe Asp Val Gln Asn Pro Gly Asp Lys Phe Asn Asn
               125                 130                 135

Asp Ala His Lys Tyr Cys Ala Leu Ser Asn Asp Ser Ser Lys Thr
               140                 145                 150

Met Lys Ser Gly Lys Phe Val Phe Leu Lys Asn Glu Gly Leu Ser
               155                 160                 165

Asp Ile Ser Leu Met Leu Asn Val Cys Tyr Asp Ile Ile Asn Lys
               170                 175                 180

Arg Met Pro Phe Ser Pro Tyr Ile Cys Ala Gly Ile Gly Thr Asp
               185                 190                 195

Leu Ile Phe Met Phe Asp Ala Ile Asn His Lys Ala Ala Tyr Gln
               200                 205                 210

Gly Lys Leu Gly Phe Asn Tyr Pro Ile Ser Pro Glu Ala Asn Ile
               215                 220                 225

Ser Met Gly Val His Phe His Lys Val Thr Asn Asn Glu Phe Arg
               230                 235                 240

Val Pro Val Leu Leu Thr Ala Gly Gly Leu Ala Pro Asp Asn Leu
               245                 250                 255

Phe Ala Ile Val Lys Leu Ser Ile Cys His Phe Gly Leu Glu Phe
               260                 265                 270

Gly Tyr Arg Val Ser Phe
               275
```

<210> SEQ ID NO 45
<211> LENGTH: 813

-continued

<212> TYPE: DNA
<213> ORGANISM: Ehrlichia canis
<220> FEATURE:
<223> OTHER INFORMATION: nucleic acid sequence of E. canis p28-9

<400> SEQUENCE: 45

```
atgaattaca aaagatttgt tgtaggtgtt acgctgagta catttgtttt tttcttatct     60
gatggtgctt tttctgatgc aaatttttct gaagggagga gaggacttta tataggtagt    120
cagtataaag ttggtattcc caattttagt aatttttcag ctgaagaaac aattcctggt    180
attacaaaaa agatttttgc gttaggtctt gataagtctg agataaatac tcacagcaat    240
tttacacgat catatgaccc tacttatgca agcagttttg cagggtttag tggtatcatt    300
ggatattatg ttaatgactt tagggtagaa tttgaaggtt cttatgagaa ttttgaacct    360
gaaagacaat ggtaccctga gaatagccaa agctacaaat tttttgcttt gtctcgaaat    420
gctacaaata gtgataataa gtttatagta ctagagaata acggcgttgt tgacaagtct    480
cttaatgtaa atgtttgtta tgatattgct agtggtagta ttcctttagc accttatatg    540
tgtgctggtg ttggtgcaga ttatataaag tttttaggta tatcattgcc taagttttct    600
tatcaagtta agtttggtgt caactaccct ctaaatgtta atactatgtt gtttggtggg    660
ggttattacc ataaggttgt aggtgatagg catgagagag tagaaatagc ttaccatcct    720
actgcattat ctgacgttcc tagaactact tcagcttctg ctactttaaa tactgattat    780
tttggttggg agattggatt tagatttgcg cta                                 813
```

<210> SEQ ID NO 46
<211> LENGTH: 271
<212> TYPE: PRT
<213> ORGANISM: Ehrlichia canis
<220> FEATURE:
<223> OTHER INFORMATION: amino acid sequence of E. canis p28-9 protein

<400> SEQUENCE: 46

```
Met Asn Tyr Lys Arg Phe Val Val Gly Val Thr Leu Ser Thr Phe
                5                   10                  15

Val Phe Phe Leu Ser Asp Gly Ala Phe Ser Asp Ala Asn Phe Ser
                20                  25                  30

Glu Gly Arg Arg Gly Leu Tyr Ile Gly Ser Gln Tyr Lys Val Gly
                35                  40                  45

Ile Pro Asn Phe Ser Asn Phe Ser Ala Glu Glu Thr Ile Pro Gly
                50                  55                  60

Ile Thr Lys Lys Ile Phe Ala Leu Gly Leu Asp Lys Ser Glu Ile
                65                  70                  75

Asn Thr His Ser Asn Phe Thr Arg Ser Tyr Asp Pro Thr Tyr Ala
                80                  85                  90

Ser Ser Phe Ala Gly Phe Ser Gly Ile Ile Gly Tyr Tyr Val Asn
                95                  100                 105

Asp Phe Arg Val Glu Phe Glu Gly Ser Tyr Glu Asn Phe Glu Pro
                110                 115                 120

Glu Arg Gln Trp Tyr Pro Glu Asn Ser Gln Ser Tyr Lys Phe Phe
                125                 130                 135

Ala Leu Ser Arg Asn Ala Thr Asn Ser Asp Asn Lys Phe Ile Val
                140                 145                 150

Leu Glu Asn Asn Gly Val Val Asp Lys Ser Leu Asn Val Asn Val
                155                 160                 165

Cys Tyr Asp Ile Ala Ser Gly Ser Ile Pro Leu Ala Pro Tyr Met
```

```
                        170                 175                 180
Cys Ala Gly Val Gly Ala Asp Tyr Ile Lys Phe Leu Gly Ile Ser
                    185                 190                 195
Leu Pro Lys Phe Ser Tyr Gln Val Lys Phe Gly Val Asn Tyr Pro
                    200                 205                 210
Leu Asn Val Asn Thr Met Leu Phe Gly Gly Tyr Tyr His Lys
                    215                 220                 225
Val Val Gly Asp Arg His Glu Arg Val Glu Ile Ala Tyr His Pro
                    230                 235                 240
Thr Ala Leu Ser Asp Val Pro Arg Thr Thr Ser Ala Ser Ala Thr
                    245                 250                 255
Leu Asn Thr Asp Tyr Phe Gly Trp Glu Ile Gly Phe Arg Phe Ala
                    260                 265                 270
Leu
271
```